United States Patent
Ambrosina et al.

(10) Patent No.: US 11,542,936 B2
(45) Date of Patent: *Jan. 3, 2023

(54) FLUID FLOW CONTROL AND DELIVERY VIA MULTIPLE FLUID PUMPS

(71) Applicant: Fresenius Kabi USA, LLC, Lake Zurich, IL (US)

(72) Inventors: Jesse E. Ambrosina, Topsfield, MA (US); Benjamin G. Powers, Portsmouth, NH (US)

(73) Assignee: Fresenius Kabi USA, LLC, Lake Zurich, IL (US)

( * ) Notice: Subject to any disclaimer, the term of this patent is extended or adjusted under 35 U.S.C. 154(b) by 506 days.

This patent is subject to a terminal disclaimer.

(21) Appl. No.: 15/468,558

(22) Filed: Mar. 24, 2017

(65) Prior Publication Data

US 2018/0274533 A1    Sep. 27, 2018

(51) Int. Cl.
*F04B 49/08* (2006.01)
*F04B 43/06* (2006.01)
(Continued)

(52) U.S. Cl.
CPC .............. *F04B 49/08* (2013.01); *F04B 23/08* (2013.01); *F04B 23/10* (2013.01); *F04B 43/06* (2013.01);
(Continued)

(58) Field of Classification Search
CPC .... F04B 43/073; F04B 53/20; F04B 2205/09; F04B 13/00; F04B 23/06; F04B 43/12;
(Continued)

(56) References Cited

U.S. PATENT DOCUMENTS

| 3,496,878 A | 2/1970 | Hargest et al. |
| 4,290,346 A | 9/1981 | Bujan |

(Continued)

FOREIGN PATENT DOCUMENTS

| EP | 2724736 A1 | 4/2014 |
| WO | 0176518 A1 | 10/2001 |

(Continued)

OTHER PUBLICATIONS

International Search Report for PCT/US2014/014467; dated May 19, 2014; 2 pages.
(Continued)

*Primary Examiner* — Kenneth J Hansen
*Assistant Examiner* — Benjamin Doyle
(74) *Attorney, Agent, or Firm* — Armis IP Law, LLC

(57) ABSTRACT

A fluid delivery apparatus includes controller hardware, a diaphragm pump, a positive displacement pump, and a fluid conduit extending between the diaphragm pump and the positive displacement pump. During operation, and delivering fluid to a downstream recipient, the controller hardware draws fluid into a chamber of the diaphragm pump from a fluid source container. The controller hardware applies pressure to the chamber of the diaphragm pump to output the fluid in the chamber of the diaphragm pump downstream through the fluid conduit to the positive displacement pump. During application of the pressure to the chamber and outputting the fluid in the chamber of the diaphragm pump downstream, the controller hardware activates the positive displacement pump to pump the fluid from the positive displacement pump to the downstream recipient.

35 Claims, 16 Drawing Sheets

(51) Int. Cl.
  *F04B 43/12* (2006.01)
  *F04B 23/08* (2006.01)
  *F04B 49/06* (2006.01)
  *F04B 23/10* (2006.01)
  *F04B 43/14* (2006.01)

(52) U.S. Cl.
  CPC .............. *F04B 43/12* (2013.01); *F04B 43/14* (2013.01); *F04B 49/065* (2013.01); *F04B 2205/03* (2013.01); *F04B 2205/09* (2013.01)

(58) Field of Classification Search
  CPC ........ F04B 49/065; F04B 53/22; F04B 23/04; F04B 23/08; F04B 23/10; F05B 2210/30; A61M 2205/3334; A61M 1/1601; A61M 2205/50; A61M 1/16; A61M 2205/3379
  USPC ........................................................ 417/205
  See application file for complete search history.

(56) References Cited

U.S. PATENT DOCUMENTS

| | | | |
|---|---|---|---|
| 4,337,639 A | 7/1982 | Jackson | |
| 4,976,162 A | 12/1990 | Kamen | |
| 5,421,208 A | 6/1995 | Packard et al. | |
| 5,474,683 A | 12/1995 | Bryant et al. | |
| 6,604,908 B1 | 8/2003 | Bryant et al. | |
| 6,731,971 B2* | 5/2004 | Evans, III | A61M 5/007 600/431 |
| 7,313,431 B2* | 12/2007 | Uber, III | G16H 40/63 600/431 |
| 7,654,982 B2 | 2/2010 | Carlisle et al. | |
| 8,594,954 B2 | 11/2013 | Macron et al. | |
| 9,517,295 B2* | 12/2016 | Wilt | A61M 1/16 |
| 2002/0026148 A1* | 2/2002 | Uber, III | A61M 5/16827 604/247 |
| 2002/0182090 A1 | 12/2002 | Gray | |
| 2003/0220605 A1* | 11/2003 | Bowman, Jr. | A61M 5/145 264/109 |
| 2005/0118048 A1* | 6/2005 | Traxinger | A61M 1/0058 417/477.2 |
| 2005/0131332 A1* | 6/2005 | Kelly | A61M 1/3656 604/4.01 |
| 2006/0079809 A1* | 4/2006 | Goldberger | A61B 5/150366 600/576 |
| 2007/0219496 A1* | 9/2007 | Kamen | A61M 5/168 604/131 |
| 2007/0264130 A1 | 11/2007 | Mallett | |
| 2008/0175719 A1* | 7/2008 | Tracey | F04B 39/12 417/474 |
| 2009/0131863 A1 | 5/2009 | Carlisle et al. | |
| 2010/0040483 A1* | 2/2010 | Berger | G01N 30/32 417/205 |
| 2011/0028937 A1 | 2/2011 | Powers et al. | |
| 2011/0160649 A1 | 6/2011 | Pan | |
| 2011/0168270 A1 | 7/2011 | Carlisle et al. | |
| 2011/0218486 A1 | 9/2011 | Huitt et al. | |
| 2011/0254686 A1 | 10/2011 | Kalpin | |
| 2012/0123322 A1 | 5/2012 | Scarpaci et al. | |
| 2012/0312726 A1* | 12/2012 | Gagel | G01F 1/74 702/47 |
| 2013/0165847 A1 | 6/2013 | Scarpaci et al. | |
| 2013/0291952 A1 | 11/2013 | Zhou | |
| 2014/0216560 A1* | 8/2014 | Ambrosina | A61M 5/172 137/12 |
| 2014/0299544 A1* | 10/2014 | Wilt | A61M 1/1601 417/474 |
| 2015/0088094 A1* | 3/2015 | Gray | A61M 5/1407 604/67 |
| 2016/0151554 A1* | 6/2016 | Jansson | A61M 1/1647 700/282 |
| 2016/0354535 A1* | 12/2016 | Blott | A61F 13/02 |
| 2020/0088186 A1* | 3/2020 | Ambrosina | F04B 53/20 |

FOREIGN PATENT DOCUMENTS

| | | |
|---|---|---|
| WO | 2009094590 A2 | 7/2009 |
| WO | 2015/144628 A2 | 1/2015 |

OTHER PUBLICATIONS

Supplementary European Search Report for EP14749592; date of completion Jan. 19, 2016; 2 pages.
International Search Report for PCT/US2018/023080 dated Jun. 28, 2018; 2 pages.
Supplementary European Search Report, EP 18 77 1628, dated Jul. 23, 2020, pp. 12.

* cited by examiner

FLUID FLOW CONTROL AND DELIVERY VIA MULTIPLE FLUID PUMPS

BACKGROUND

Conventional techniques of delivering fluid to a recipient (such as a patient in a hospital or other patient care setting) using a diaphragm pump can include drawing a fluid from a fluid source into a chamber of a diaphragm pump via application of negative pressure. After the chamber is filled, a respective fluid delivery system applies a positive pressure to the chamber causing the fluid in the chamber to be delivered to a corresponding patient. The rate at which the fluid is delivered to the recipient may vary depending upon the magnitude of the positive pressure applied to the chamber. Eventually, after applying the positive pressure to the chamber for a sufficient amount of time, the fluid in the chamber is depleted and the chamber is refilled using negative pressure again.

In most applications, the amount of fluid drawn into the chamber of the diaphragm pump is substantially less than the total amount of fluid intended to be delivered to the patient. To deliver the appropriate amount of fluid to the patient over time, after emptying a previously filled chamber, the fluid delivery system repeats the cycle of drawing fluid from the fluid source into the chamber, and then applying positive pressure to the chamber to deliver the fluid to the recipient.

According to conventional use of diaphragm pumps, based on the amount of elapsed time between time successive operations of drawing fluid into the chamber and completely expelling the fluid out of the chamber in the diaphragm pump, the fluid delivery system is able to determine the rate at which fluid is delivered to a corresponding patient.

As previously discussed, one type of fluid pump is a conventional diaphragm pump. Typically, during use, a negative pressure is applied to the conventional diaphragm pump to draw fluid into a respective fluid chamber. Thereafter, a positive pressure is then applied to the conventional diaphragm pump to expel the fluid from the fluid chamber.

Another type of fluid pump is a conventional peristaltic pump. A peristaltic pump is a type of positive displacement pump used for pumping a variety of fluids. The fluid is contained within a flexible tube fitted inside a circular pump casing (though linear peristaltic pumps have been made). A rotor with a number of "rollers", "shoes", "wipers", or "lobes" attached to the external circumference of the rotor compresses the flexible tube. As the rotor turns, the part of the tube under compression is pinched closed (or "occludes"), thus forcing the fluid to be pumped to a recipient. Additionally, as the tube opens to its natural state after the passing of the cam ("restitution" or "resilience") fluid flow is induced to the pump.

Most currently available pumps used in healthcare such as infusion pumps and dialysis machines are open-loop, positive displacement style pumps. These conventional types of pumps are calibrated at fixed known conditions. If the actual conditions of use vary from the calibration conditions, the actual fluid delivery rate can deviate significantly from a desired flow rate. Since there is no way of measuring fluid flow in such systems, there is no way for a user to know whether there is a problem with the fluid flow rate. Flow rate of these types of conventional pumps can be affected by changes in inlet pressure (e.g., the height of the fluid source above the pump), outlet or back pressure (e.g., down stream flow restrictions from small diameter catheters), fluid viscosity (e.g. packed red blood is 16× the viscosity of saline). These and other environmental factors can drastically affect the operation of positive displacement pumps.

BRIEF DESCRIPTION OF EMBODIMENTS

A significant drawback of some conventional fluid pumps is that they have no way to monitor and/or measure the actual flow rate of the fluid being delivered to the patient.

One way to measure the flow rate of fluid to a recipient is to use a conventional flow rate sensor. The main difficulty with implementing a flow rate sensor to measure flow is the very large required dynamic range required to accurately detect delivery of fluid at different rates. For example, in certain instances, it is desirable that intravenous pumps operate from as low as 0.1 ml/hr to as high as 1200 ml/hr or more. This is at least a dynamic range of 10,000 to 1, which is far beyond the capabilities of most conventional sensors and measurement technologies.

Another requirement of conventional flow sensor technology used for the delivery of fluid is that the delivered fluid must be completely contained within a sterile disposable assembly. No fluid can directly contact the sensor, or, if the fluid does contact the sensor, the sensor must be thrown away after use due to contamination. Thus, implementing a disposable sensor capable of precisely measuring flow rates over the desired operating range can be cost prohibitive.

Another limitation of conventional flow sensor technology is that intravenous fluids and medications are constantly changing and evolving over time. The user, and therefore the delivery system, has no knowledge of the unique fluid properties of the fluid being delivered. Therefore, a flow measurement system cannot practically use or depend on the thermal, optical, or density (viscosity) characteristics of the type of fluid to be dispensed.

Embodiments herein provide novel and improved fluid delivery over conventional techniques.

More specifically, in accordance with one or more embodiments, a fluid delivery apparatus includes controller hardware, a pneumatically (gas) driven diaphragm pump, pump, a downstream pump (such as a positive displacement pump), and a fluid conduit (fluid tight pathway to convey fluid) extending between the diaphragm pump through the positive displacement pump to a recipient. The diaphragm pump can be configured to receive the fluid from a remotely located fluid source. Accordingly, embodiments herein include a pressure controlled variable displacement pump (such as a diaphragm pump) feeding a variable positive displacement pump (such as a rotary peristaltic pump, linear peristaltic pump, rotary lobe pump, progressive cavity pump, rotary gear pump, piston pump, diaphragm pump, screw pump, gear pump, hydraulic pump, rotary vane pump, etc.).

During operation of delivering fluid to a recipient, the controller hardware initially draws fluid into a chamber of the diaphragm pump through the application of negative pressure. Subsequent to filling the chamber, the controller hardware applies positive pressure to the chamber of the diaphragm pump to output the fluid in the chamber (of the diaphragm pump) downstream through the fluid conduit to the positive displacement pump. The positive displacement pump delivers fluid received from the diaphragm pump to a recipient.

In accordance with further embodiments, a pressure of the fluid in a first portion of the fluid conduit upstream of the positive displacement pump between the positive displacement pump (that pinches, occludes, controls, etc., a flow of the fluid) and the diaphragm pump is greater than a pressure of the fluid in a second portion of the fluid conduit downstream of the positive displacement pump.

In accordance with further embodiments, a pressure of the fluid in a first portion of the fluid conduit upstream of the positive displacement pump between the positive displacement pump (that pinches a flow of the fluid) and the diaphragm pump is less than a pressure of the fluid in a second portion of the fluid conduit downstream of the positive displacement pump.

In accordance with another embodiment, the controller hardware of the fluid delivery apparatus as described herein is further operable to: measure a rate of fluid expelled from the chamber of the diaphragm pump downstream to the positive displacement pump. In one embodiment, the controller hardware uses a measured rate of expelled fluid from the chamber to control a rate of delivering fluid from the positive displacement pump to the recipient.

The flow rate of fluid through the diaphragm pump can be measured in any suitable manner. For example, in one embodiment, the controller hardware is further operable to: cyclically receive (draw), over each of multiple cycles, a quantum of the fluid from a disparately located fluid source container into the chamber of the diaphragm pump at each of multiple fill times.

In one embodiment, the controller hardware applies a negative pressure to the chamber of the diaphragm pump to draw the fluid from the fluid source container. If desired, the controller hardware can be configured to draw the fluid from the fluid source container into the chamber of the diaphragm pump during a condition in which the positive displacement pump blocks a flow of the fluid received from the diaphragm pump through the positive displacement pump to the recipient. Thus, because the positive displacement pump blocks fluid flow, instead of drawing fluid in a direction from the positive displacement pump, the diaphragm pump draws the fluid from the upstream fluid source container.

In accordance with further embodiments, forces of gravity can be used as a way to fill the chamber of the diaphragm pump. For example, the container of fluid can be disposed above the diaphragm pump. Accordingly, negative pressure may not be needed to draw fluid into the chamber.

As previously discussed, subsequent to drawing the fluid into the chamber of the diaphragm pump, the controller hardware applies pressure to the chamber of the diaphragm pump to deliver the fluid in the chamber downstream to the positive displacement pump.

In yet further embodiments, to provide precise fluid flow control over a large possible range, the controller hardware measures a flow rate of fluid delivered to the recipient based upon measurements of remaining portions of fluid in the chamber over time. For example, in one embodiment, the controller hardware is operable to measure a flow rate of the fluid expelled from the chamber of the diaphragm pump downstream to the positive displacement pump. As previously discussed, the positive displacement pump controllably blocks a flow of the fluid received from the diaphragm pump to the recipient. The controller hardware utilizes the measured flow rate of the fluid (as detected from measuring respective remaining portions of fluid in the chamber of the diaphragm pump) to control a rate of delivering fluid from the positive displacement pump to the recipient.

If the measurement of fluid flowing through the diaphragm pump is greater than the desired flow rate setting, the controller hardware decreases the rate of delivering fluid form the positive displacement pump to the recipient. Conversely, if the measurement of the fluid flowing through the diaphragm pump as detected by the controller hardware is less than the desired flow rate setting, the controller hardware increases the rate of delivering fluid from the positive displacement pump to the recipient. Accordingly, in one embodiment, the measured rate of fluid flow through the diaphragm pump can be used as a basis to control a downstream positive displacement pump to provide accurate fluid flow.

In accordance with yet further embodiments, the controller hardware, at each of multiple measurement times between a first time of filling of the chamber and a next successive time of filling the fluid into the chamber from a fluid source, temporarily changes a magnitude of the pressure at each of multiple sample windows to the chamber of the diaphragm pump to measure a rate of delivering the fluid from the chamber downstream to the segment. More specifically, according to one embodiment, the controller hardware further controls the positive displacement pump to provide corresponding continuous flow of fluid from the positive displacement pump to the recipient in a time window in which the magnitude of pressure in the diaphragm pump is temporarily modified to measure a delivery rate of fluid to the positive displacement pump. During each of multiple measurement windows in the time window, the controller hardware measures a respective portion of fluid remaining in the diaphragm pump to determine a respective fluid flow rate.

The controller hardware utilizes the respective measured portions of fluid remaining in the diaphragm pump as measured during the multiple measurement windows to calculate a rate of fluid delivered by the positive displacement pump to the recipient. As previously discussed, in one embodiment, the positive displacement pump can be configured to include a corresponding mechanical pump element that controls an amount of the fluid delivered by the positive displacement pump to a recipient.

Embodiments herein (such as the combination of a diaphragm pump to measure a fluid delivery rate and a positive displacement pump to control physical transfer of fluid to a recipient) are advantageous over conventional techniques. For example, according to embodiments herein, inclusion of a diaphragm pump: i) provides a way to measure a flow rate of fluid, ii) provides a way (using negative pressure) to draw fluid from a source above or below the pump, and iii) provides a constant and reliable pressure of fluid to the inlet of a positive displacement pump. The fluid delivery apparatus and corresponding methods as described herein also provide one or more of the following advantages over conventional techniques: i) fast start and stop time to reach desired delivery flow rate set point, ii) large dynamic range to control flow rates from 0.1 or lower to 1200 or higher, iii) flow rate control that is immune to inlet or outlet pressure changes, iv) flow rate control that is immune to large variations in fluid properties (such as viscosity), real-time flow measurement for improved safety, and so on.

These and other more specific embodiments are disclosed in more detail below.

Note that any of the resources as discussed herein can include one or more computerized devices, fluid delivery systems, servers, base stations, wireless communication equipment, communication management systems, workstations, handheld or laptop computers, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations summarized above and disclosed in detail below. One such embodiment comprises a computer program product including a non-transitory computer-readable storage medium (i.e., any physical computer readable hardware storage medium) on which software instructions are encoded for subsequent execution. The instructions, when executed in a computerized device (e.g., computer processing hardware) having a processor, program and/or cause the processor to perform the operations disclosed herein. Such arrangements are typically provided as software, code, instructions, and/or other data (e.g., data structures) arranged or encoded on a non-transitory computer readable storage medium such as an optical medium (e.g., CD-ROM), floppy disk, hard disk, memory stick, etc., or other a medium such as firmware or shortcode in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

One embodiment herein includes a computer readable storage medium and/or system having instructions stored thereon. The instructions, when executed by computer processor hardware, cause the computer processor hardware to: draw fluid into a chamber of the diaphragm pump; apply pressure to the chamber of the diaphragm pump to output the fluid in the chamber of the diaphragm pump downstream through the fluid conduit to a positive displacement pump; and during application of the pressure to the chamber and outputting the fluid in the chamber downstream, activate the positive displacement pump to pump the fluid from the positive displacement pump to a recipient.

The ordering of the operations above has been added for clarity sake. Note that any of the processing steps as discussed herein can be performed in any suitable order.

Other embodiments of the present disclosure include software programs and/or respective hardware to perform any of the operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or within a software application.

As discussed herein, techniques herein are well suited for use in delivering fluid to any suitable target recipient. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

Figure 1:
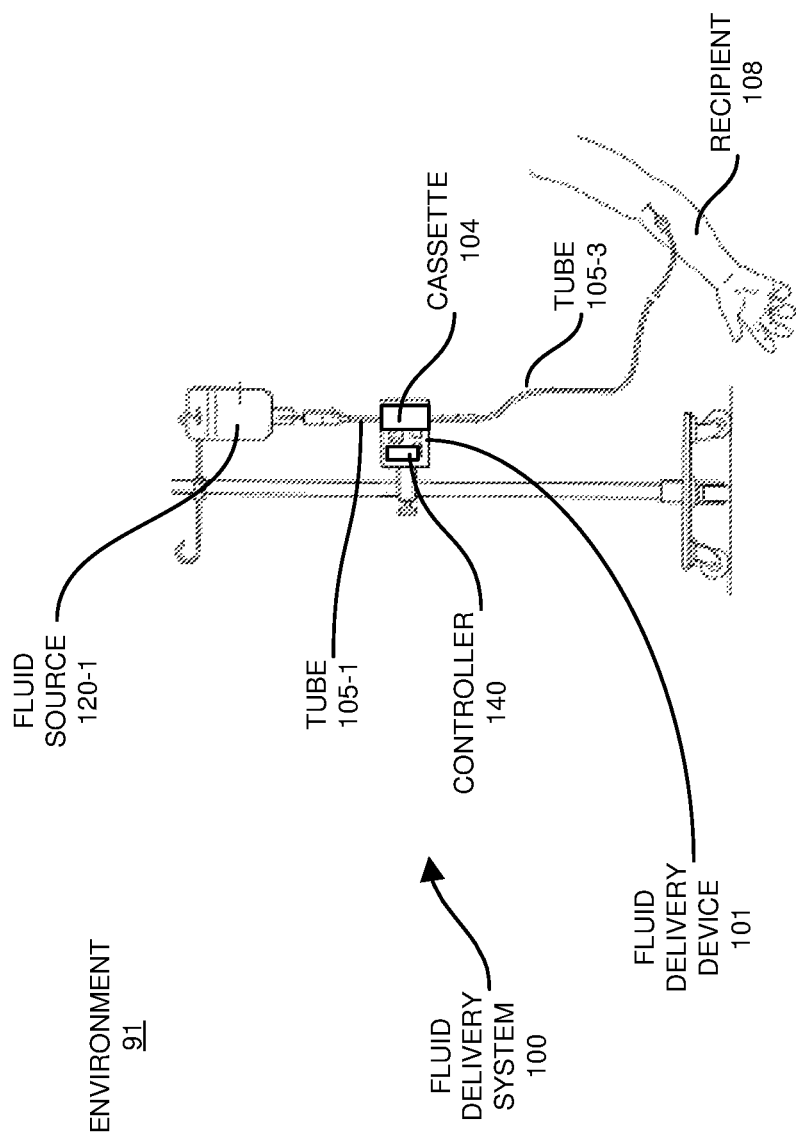
FIG. 1 is an example diagram illustrating a fluid delivery system according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

As previously discussed, in one embodiment, a fluid delivery apparatus includes controller hardware, a diaphragm pump, a positive displacement pump, and a fluid conduit extending between the diaphragm pump and the positive displacement pump. During operation, and delivering fluid to a downstream recipient, the controller hardware draws fluid into a chamber of the diaphragm pump. The controller hardware applies pressure to the chamber of the diaphragm pump to output the fluid in the chamber of the diaphragm pump downstream through the fluid conduit to the positive displacement pump. During application of the pressure to the chamber and outputting the fluid in the chamber downstream to the positive displacement pump, the controller hardware activates the positive displacement pump to pump the fluid in the segment from the positive displacement pump to the downstream recipient.

Now, more specifically, FIG. 1 is an example diagram illustrating a fluid delivery system according to embodiments herein.

As shown, fluid delivery environment 91 includes fluid delivery system 100. Fluid delivery system 100 includes fluid source 120-1 that stores fluid for delivery to the recipient 108.

In one embodiment, the cassette 104 is a disposable cartridge inserted into a cavity of a housing of the fluid delivery device 101 associated with fluid delivery system 100. During delivery, fluid from the fluid source 120-1 is limited to contacting disposable tube set including cassette 104, tubes 103, and its corresponding components as further discussed below. When delivering fluid to a different patient, a caregiver inserts a new cassette into the cavity of fluid delivery system 100. The new cassette includes a corresponding set of new (sterile) tubes.

Thus, the fluid delivery system 100 can be used for many patients without having to be cleaned; a new cassette is used for each delivered fluid.

As mentioned, during operation, the controller 140 of fluid delivery system 100 controls delivery of fluid from a source 120-1 to recipient 108 (such as a patient or other suitable target). Tube 105-1 (fluid conduit) conveys fluid from fluid source 120-1 to cassette 104. Tube 105-3 conveys fluid from cassette 104 to recipient 108.

The controller 140 controls one or more components in cassette 104 to deliver fluid received from fluid source 120-1 through tube 105-3 to recipient 108.

Figure 2:
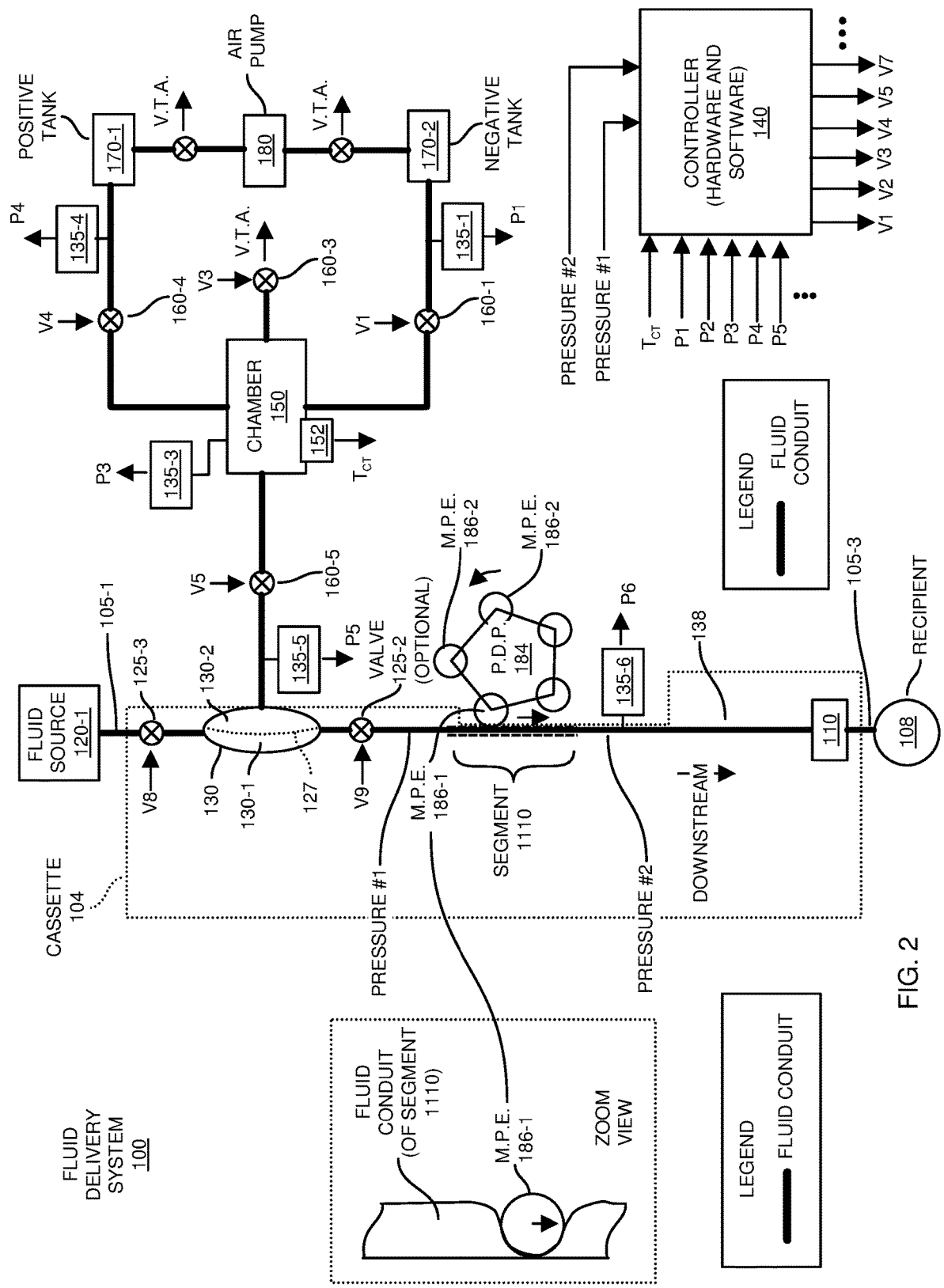
FIG. 2 is an example diagram of implementing a diaphragm pump and a positive displacement pump to deliver fluid to a respective recipient according to embodiments herein.

FIG. 2 is an example diagram of implementing a diaphragm pump and a positive displacement pump to deliver fluid to a respective recipient according to embodiments herein.

More specifically, in accordance with one or more embodiments, a fluid delivery system (apparatus, device, etc.) includes controller 140 (hardware and/or software), a diaphragm pump chamber 130, a positive displacement pump 184 (such as a rotary peristaltic pump, linear peristaltic pump, rotary lobe pump, progressive cavity pump, rotary gear pump, piston pump, diaphragm pump, screw pump, gear pump, hydraulic pump, rotary vane pump, rope pump, flexible impeller pump, etc.), and a fluid conduit (fluid conduit) extending between the diaphragm pump 130 through the positive displacement pump 184 to a recipient 108. During operation of delivering fluid to the downstream recipient 108, the controller 140 initially draws fluid into a chamber 130-1 of the diaphragm pump 130 (such as via negative gas pressure applied to chamber 130-2).

In one embodiment, the positive displacement pump is a non-pneumatically controlled pump (such as a rotary peristaltic fluid pump, linear peristaltic pump, rotary lobe pump, progressive cavity pump, rotary gear pump, piston pump, screw pump, gear pump, rotary vane pump, rope pump, flexible impeller pump, etc.). The diaphragm pump 130 is pneumatically (gas) driven and allows the controller to calculate flow rate as discussed herein.

In accordance with further embodiments, the positive displacement pump 184 can be another diaphragm pump (i.e., a pneumatically driven pump). As further described herein, subsequent to filling the chamber 130-1 with fluid from fluid source 120-1, the controller 140 applies pressure to the chamber 130-1 (such as via positive gas pressure applied to chamber 130-2) of the diaphragm pump 130 to output the fluid in the chamber 130-1 (of the diaphragm pump 130) downstream through the fluid conduit to the positive displacement pump 184.

In one embodiment, the positive displacement pump 184 is a peristaltic fluid pump. As shown, a segment 1110 of the fluid conduit of fluid delivery system 100 is an elastically deformable conduit (of any suitable material such as rubber, plastic, etc.) driven by the positive displacement pump 184. During application of the positive (gas) pressure to the chamber 130-1 (via filling chamber 130-2 with more and more gas over time) and outputting the fluid in the chamber 130-1 downstream to the positive displacement pump 184, the controller 140 activates the positive displacement pump 184 to pump the fluid disposed in a portion of the segment 1110 downstream of the mechanical pump element 186-1 (such as a roller, peristaltic pump element, non-pneumatic pump element, or other suitable element to movably compress segment 1110 filled with fluid) along the fluid conduit to the downstream recipient 108.

Accordingly, in one embodiment, a diaphragm pump 130 delivers fluid to the elastically deformable conduit (segment 1110); the controller 140 controls the positive displacement pump 184 and corresponding mechanical pump element 186-1 in a sweeping motion (in a downward direction in FIG. 2) to deliver the fluid in the segment 1110 in a downstream direction to recipient 108.

More specifically, as shown, in one embodiment, the mechanical pump element 186-1 is in contact with and pinches (and/or obstructs) the elastically deformable conduit at position #1. Via the pinching, the mechanical pump element 186-1 blocks a flow of fluid from the diaphragm pump 130 further downstream of position #1 into a portion of the segment 1110 downstream of the mechanical pump element 186-1.

Sweeping physical contact of the mechanical pump element 186-1 to the elastically deformable conduit controllably conveys fluid in the elastically deformable conduit further downstream to the recipient 108. Accordingly, in one embodiment, the mechanical pump element 186-1 performs multiple operations including: i) restricting (or holding back) a flow of the fluid received upstream of the mechanical pump element 186-1 from the diaphragm pump 130 into the segment 1110 (elastically deformable conduit) as well as ii) via the positive displacement pump 184, controlling delivery of fluid in the segment (elastically deformable conduit) downstream of the mechanical pump element 186-1 to the recipient 108 (such as a person, animal, machine, etc.).

In accordance with further embodiments, a pressure (pressure #1) of the fluid upstream of the mechanical pump element 186-1 is different than a pressure (pressure #2) of the fluid downstream of the mechanical pump element 186-1. More specifically, in one embodiment, during pumping of fluid downstream from the diaphragm pump 130 to the positive displacement pump 184, a pressure #1 of the fluid in a first portion of the fluid conduit upstream of the mechanical pump element 186-1 (which blocks a flow of the fluid via pinching/obstructing of the fluid conduit that conveys the fluid) is greater than a pressure (pressure #2) of fluid in a second portion of the fluid conduit downstream of the mechanical pump element 186-1.

Conversely, in certain instances of pumping, the recipient 108 may apply backpressure on the fluid delivered through tube 105-3. In such an instance, the pressure #1 of the fluid in a respective portion of the fluid conduit upstream of the mechanical pump element 186-1 (which blocks a flow of the fluid via pinching or obstructing of the fluid conduit that conveys the fluid) is less than a pressure (pressure #2) of fluid in a second portion of the fluid conduit downstream of the mechanical pump element 186-1. For example, while the positive displacement pump 184 pumps fluid, the recipient 108 may provide backpressure to receiving fluid from a respective outlet of fluid pathway through tube 105-3.

Figure 9:
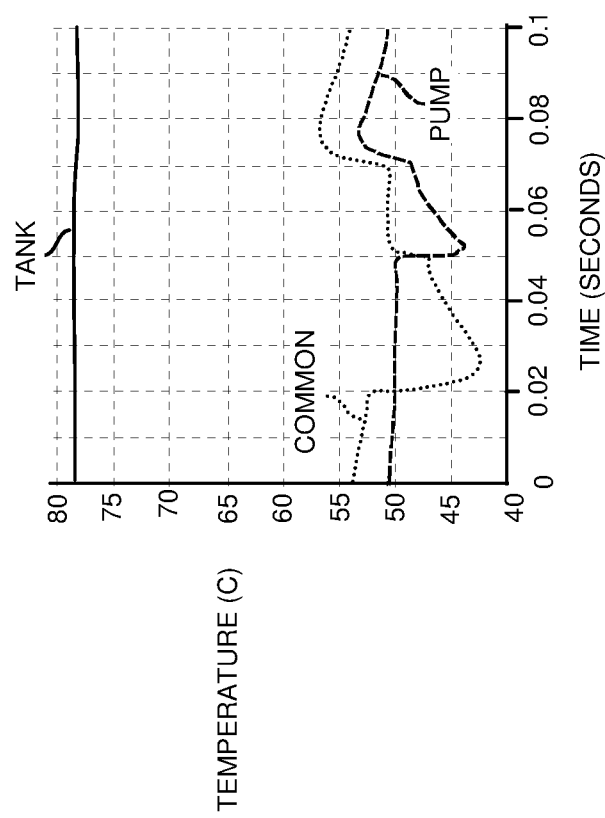
FIG. 9 is an example diagram illustrating a change in estimated gas temperatures during a fluid measurement cycle according to embodiments herein.
Figure 10A:
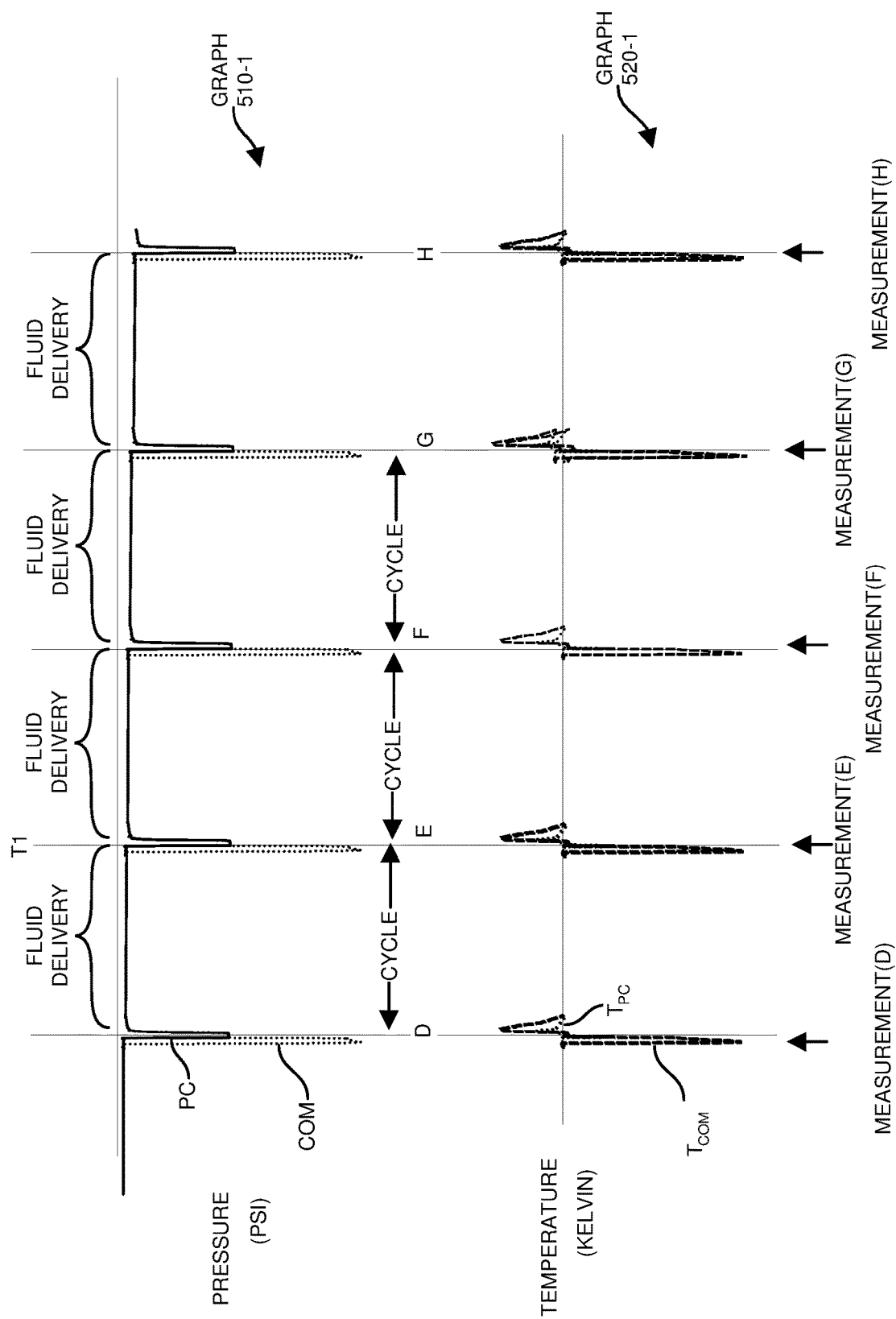
FIG. 10A is an example timing diagram illustrating application of different pressure to a diaphragm pump over time to deliver fluid to a target recipient according to embodiments herein.
Figure 10B:
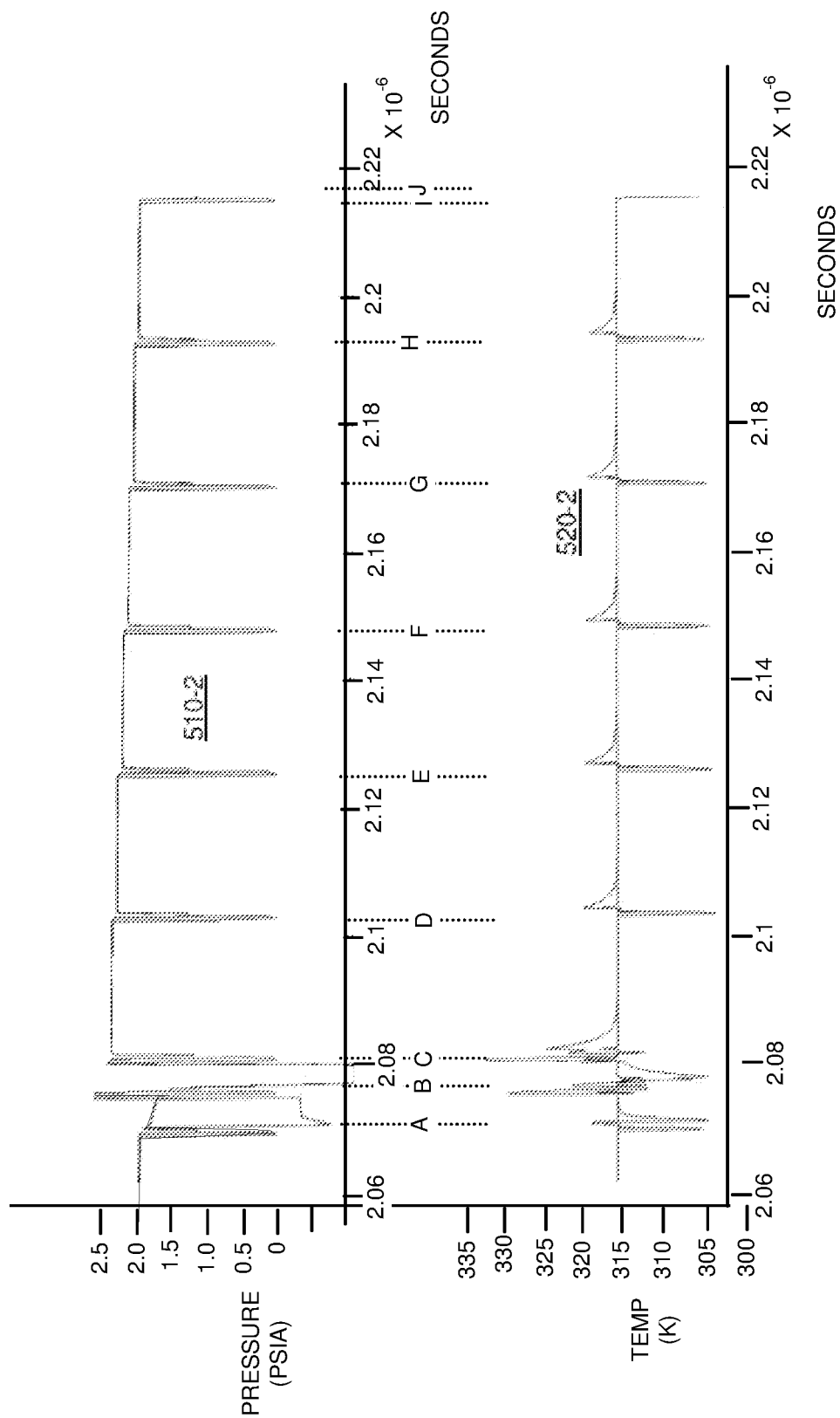
FIG. 10B is an example timing diagram illustrating application of different pressure to a diaphragm pump over time to deliver fluid to a target recipient according to embodiments herein.
Figure 11:
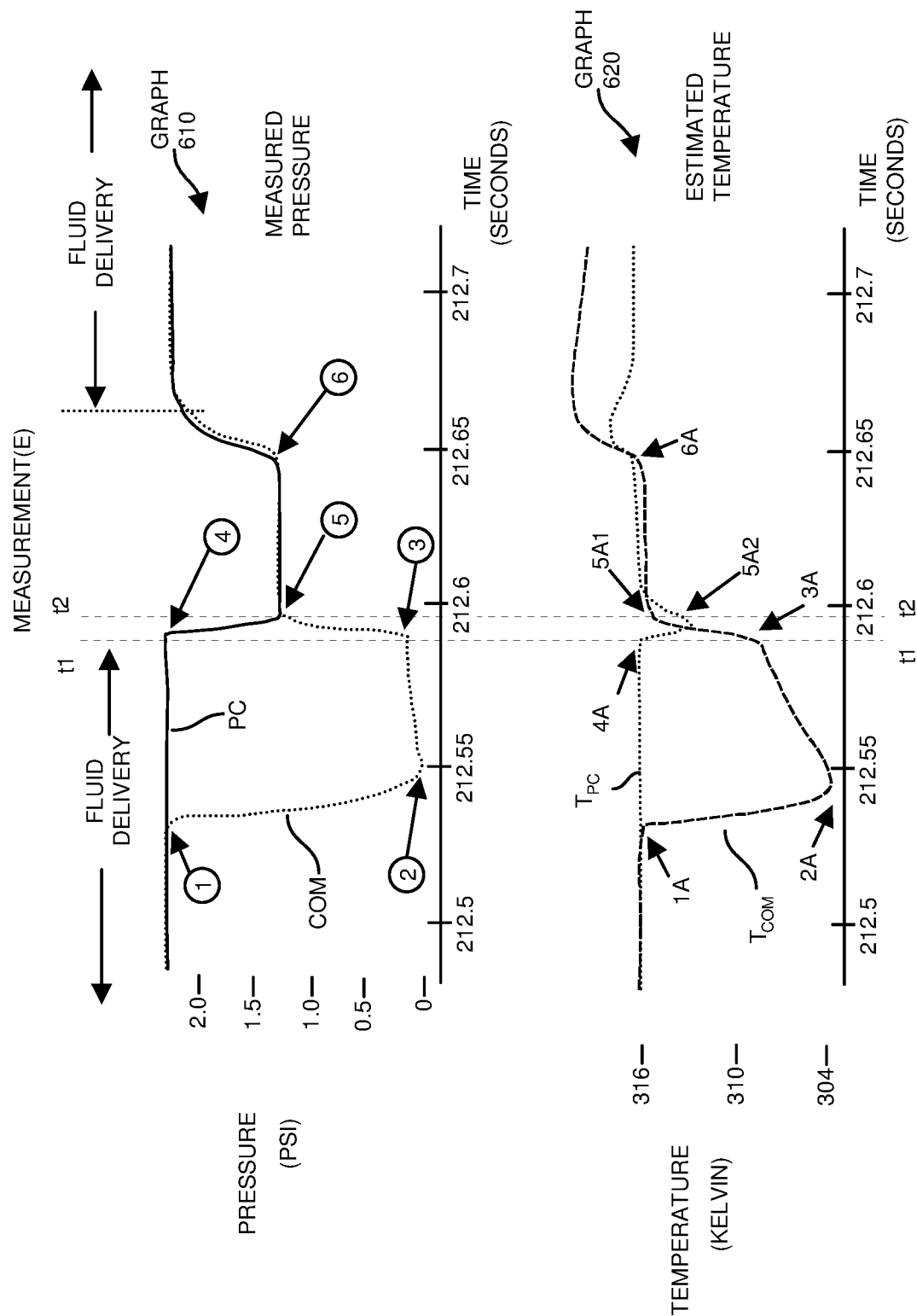
FIG. 11 is an example timing diagram illustrating temporary termination or reduction of applying positive pressure to a diaphragm pump and estimation of gas temperatures according to embodiments herein.

In accordance with another embodiment, the controller 140 of the fluid delivery apparatus as described herein is further operable to: measure (in any suitable manner) a rate of fluid expelled from the chamber 130-1 of the diaphragm pump 130 downstream to the segment of fluid conduit using techniques as discussed in subsequent FIGS. 9-15 and text. In such an instance, the controller 140 uses a measured rate of expelled fluid from the chamber 130-1 over each of multiple measurement windows (shown as measurement D, measurement E, measurement F, measurement G, measurement and H, in FIG. 10A An example of a respective measurement window is shown in FIG. 11 to control a rate of moving the mechanical pump element 186-1 to deliver the fluid to the recipient at a desired flow rate. In such an embodiment, the diaphragm pump 130 serves as an accurate way of measuring fluid delivered by the positive displacement pump 184 to the respective recipient 108.

Note that a rate of operating diaphragm pump 130 (pneumatic pump) and positive displacement pump 184 can be synchronized such that the diaphragm pump 130 delivers fluid to the segment 1110 at a substantially similar rate as the positive displacement pump 184 delivers fluid in segment 1110 downstream to the recipient 108.

As further discussed below, note that the fluid flow rate of fluid through the diaphragm pump 130 can be measured using conventional algorithms known in the art based on ideal gas laws. For example, in one embodiment, the controller 140 is further operable to: cyclically receive (draw), over each of multiple fill cycles, a quantum of the fluid from a disparately located fluid source container (such as fluid source 120-1) into the chamber 130-1 of the diaphragm pump 130 at each of multiple fill times. After each fill, as previously discussed, the controller 140 fills the chamber 130-2 with gas, which applies positive pressure to the chamber 130-1. As previously discussed, the membrane 130-1 separates the fluid in chamber 130-1 from the gas in chamber 130-2.

In one embodiment, fluid delivery system 100 includes valve 125-2. An OPEN/CLOSED setting of valve 125-2 is controlled by signal V9 generated by controller 140. Note that valve 125-2 is optional. That is, at least one of the mechanical pump elements 186 of the positive displacement pump 184 can be configured to pinch or obstruct the segment 1110 and prevent a flow of fluid through segment 1110 at any or all times.

Figure 3:
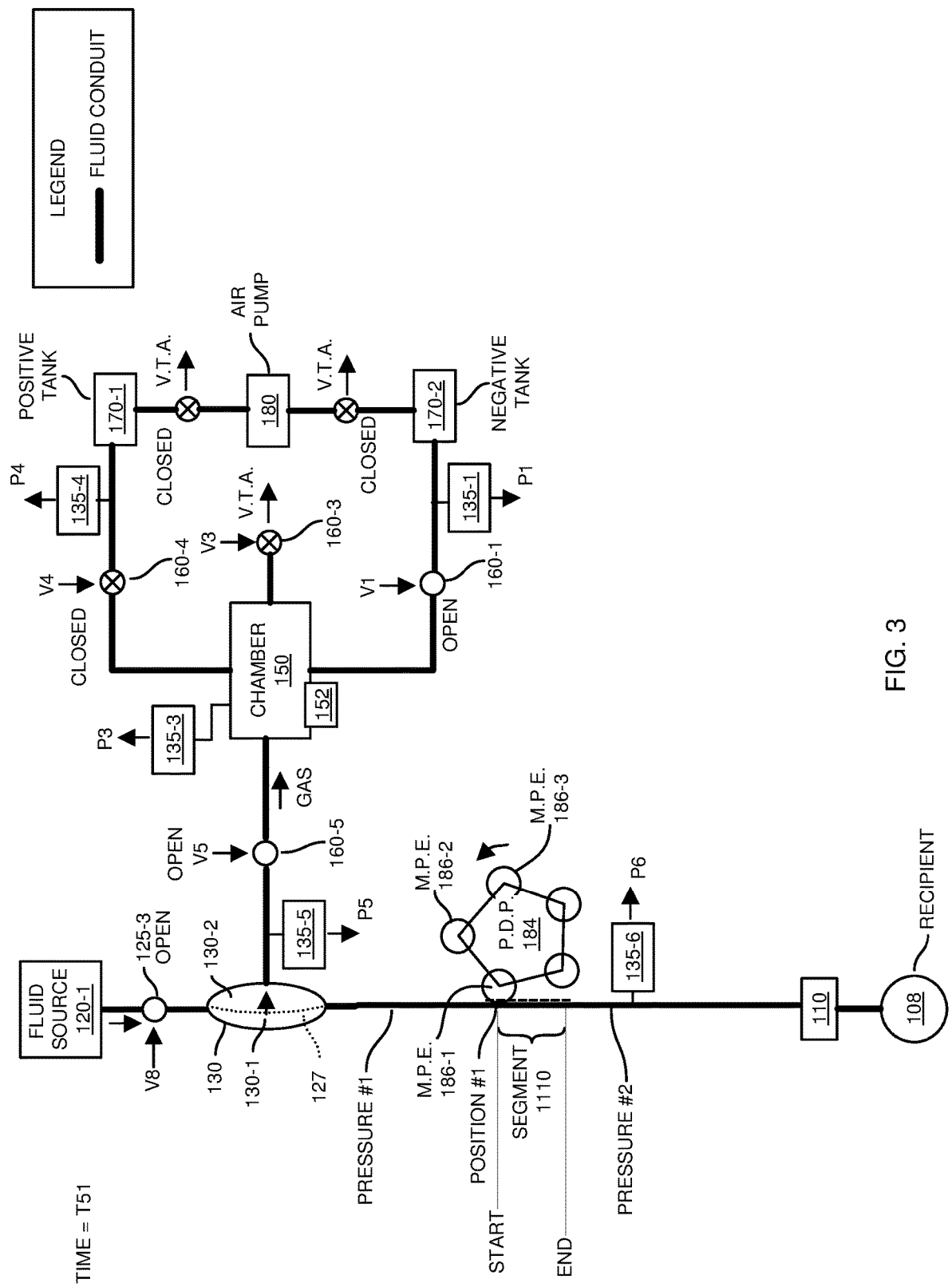
FIG. 3 is an example diagram illustrating drawing of fluid from a respective fluid source into a chamber of a diaphragm pump according to embodiments herein.

FIG. 3 is an example diagram illustrating drawing of fluid from a respective fluid source into a chamber of a diaphragm pump according to embodiments herein.

As previously discussed, the controller 140 produces respective control signals to control states of the valves to either open or closed positions. In one embodiment, while the valve 125-3 (a controllable full open or full closed valve in this embodiment) is open, valve 160-5 is open, valve 160-1 is open, while valves 160-4 and 160-3 are closed, the controller 140 applies a negative pressure (via negative tank 170-2) to the chamber 130-2 of the diaphragm pump 130. This evacuates gas from the chamber 130-2, causing the membrane 127 to draw the fluid from the fluid source 120-1 (fluid container) through valve 125-3 into chamber 130-1.

If desired, the controller 140 draws the fluid from the fluid source 120-1 into the chamber 130-1 of the diaphragm pump 130 during a condition in which mechanical pump element 186-1 of the positive displacement pump 184 (or generally the positive displacement pump 184 itself) blocks a flow of any downstream fluid being pulled backwards into the chamber 130-1. In other words, the mechanical pump element 186-1 of the positive displacement pump 184 acts as a valve in a closed position as shown in FIG. 3. Thus, instead of drawing fluid from further downstream of the elastically deformable conduit into the chamber 130-1, the application of the negative pressure to the chamber 130-2 causes the diaphragm pump 130 to draw only the fluid from the upstream fluid source 120-1 into the chamber 130-1. As previously discussed, valve 125-2 in FIG. 2 is optional.

Figure 4:
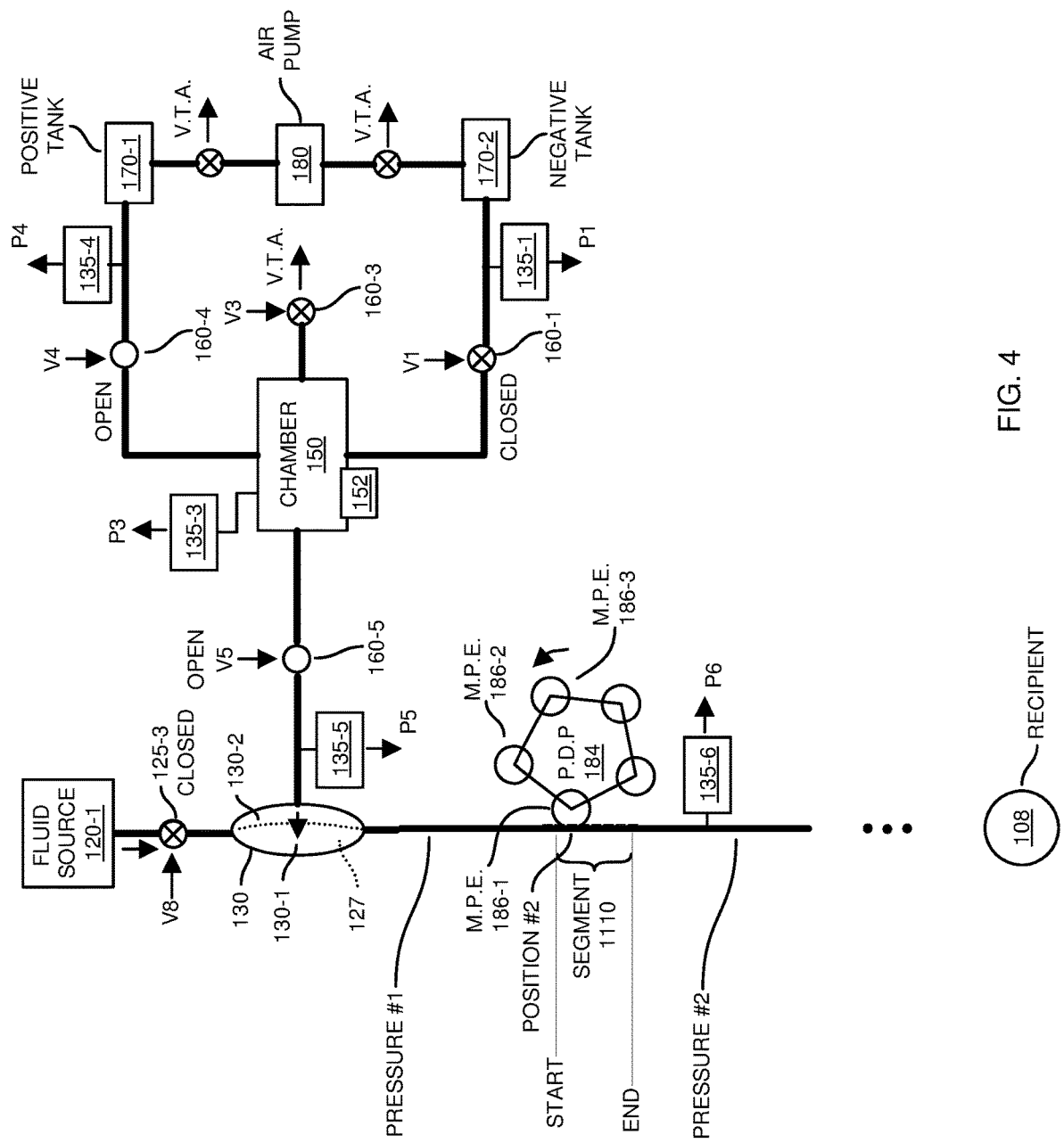
FIG. 4 is an example diagram illustrating application of positive pressure to the chamber of the diaphragm pump to convey fluid to a respective downstream positive displacement pump according to embodiments herein.

FIG. 4 is an example diagram illustrating application of positive pressure to the chamber of the diaphragm pump to convey fluid to a respective downstream positive displacement pump according to embodiments herein.

As previously discussed, subsequent to drawing the fluid into the chamber 130-1 of the diaphragm pump 130, the controller 140 closes valve 125-3 and valve 160-1 (via generation of respective control signals V8 and V1); the controller 140 opens valve 160-5 and valve 160-4 (via generation of respective control signals V5 and V4) to apply a positive gas pressure to the chamber 130-2 of the diaphragm pump 130 to deliver the fluid in the chamber 130-1 downstream to the positive displacement pump 184.

As shown, during application of positive pressure to the fluid in chamber 130-1, the mechanical pump element 186-1 of the positive displacement pump 184 controls a rate at which fluid from the diaphragm pump 130 is allowed to flow downstream into the segment 1110. As previously discussed, in addition to controlling an amount of fluid received in segment 1110 upstream of the mechanical pump element 186-1, the movement of the mechanical pump element 186-1 (in a downward direction) also controls the rate of delivering respective fluid in the segment 1110 to the recipient 108.

As previously discussed, note that the controller 140 can be configured to synchronously operate a fluid flow rate of the diaphragm pump and a fluid flow rate of the positive displacement pump 184 such that the diaphragm pump 130 delivers fluid to the segment 1110 at a substantially similar rate as the positive displacement pump 184 delivers fluid in segment 1110 downstream to the recipient 108.

Figure 5:
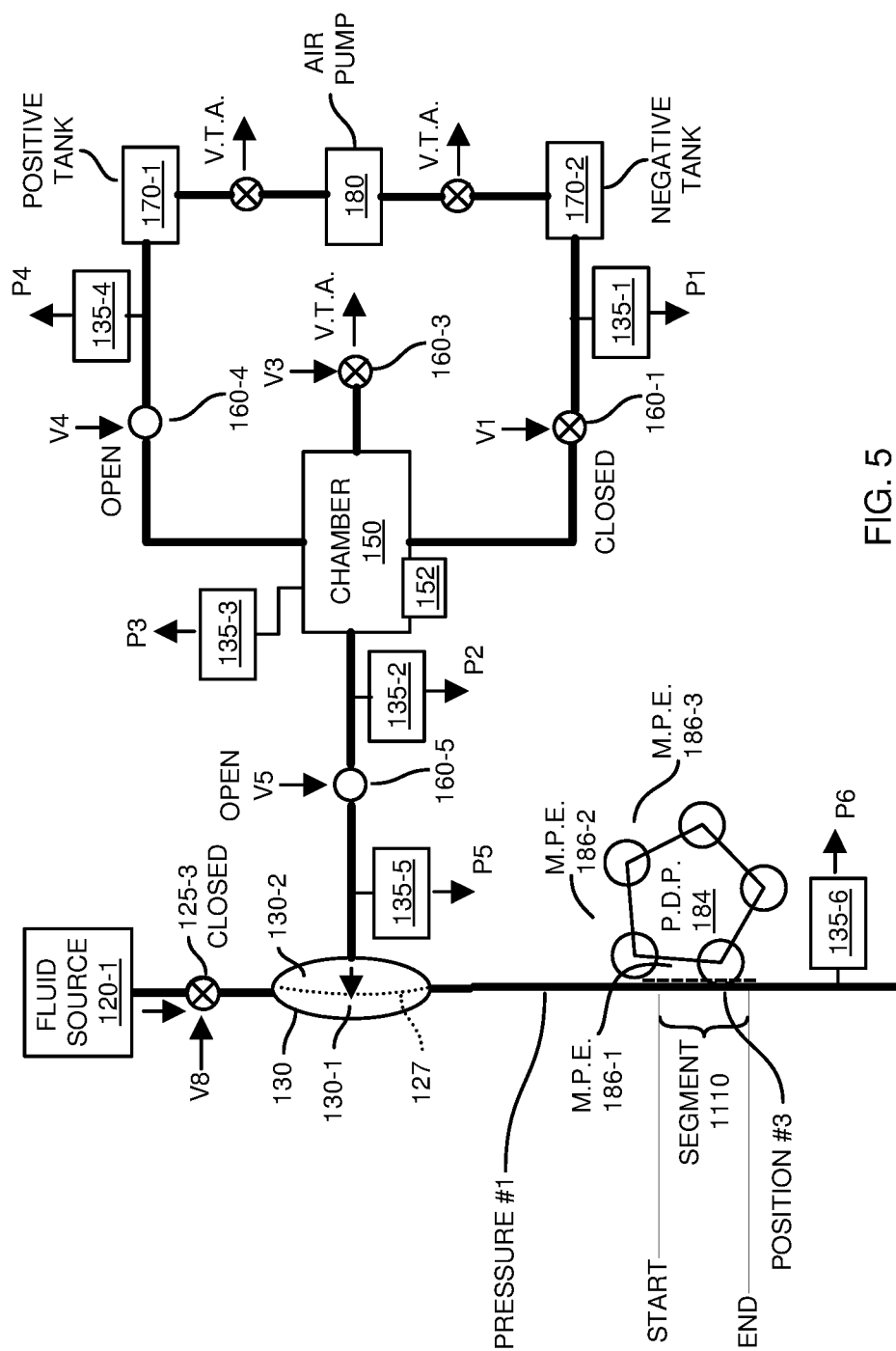
FIG. 5 is an example diagram illustrating motion of a mechanical pump element to deliver fluid (as received from a diaphragm pump) to a downstream recipient according to embodiments herein.

FIG. 5 is an example diagram illustrating continued motion of a mechanical pump element while receiving fluid from a diaphragm pump according to embodiments herein.

As shown, the positive displacement pump 184 (such as a peristaltic fluid pump) can be configured to continue to rotate over time about a respective axis (center of mechanical pump elements 186) such that when the mechanical pump element 186-1 reaches the end of the segment 1110, the next mechanical pump element 186-2 contacts the start location of segment 1110 to pinch or obstruct the segment 1110. This sets up the mechanical pump element 186-1 of the positive displacement pump 184 to start location of segment 1110. This starts a new cycle of sweeping the mechanical pump element 186-2 along segment 1110 to deliver fluid to the respective recipient 108.

As previously discussed, in one embodiment, at least one of the mechanical pump elements 186 always pinches, occludes, compresses, obstructs, etc., the segment 1110 to prevent backflow of fluid from the segment 1110 to the diaphragm pump 130. Hence, valve 125-2 may not be needed.

Note that the positive displacement pump 184 can be any type of peristaltic mechanism (rotary, linear, piston, etc.) as long as the downstream pump segment 1110 is never allowed to open and allow free flow of fluid from the diaphragm pump 130 to the recipient 108. In other words, in one embodiment, the positive displacement pump or its corresponding elements (such as mechanical pump elements 186-1, 186-2, etc.) can be configured to always occlude a flow of the fluid from the diaphragm pump 130 downstream to the recipient 108. In such an instance, the positive displacement pump 184 constantly controls the flow of fluid to the recipient 108.

Note that the ratio of volume of fluid drawn into the chamber 130-1 may be substantially the same or different than the volume of fluid in segment 1110. Accordingly, to empty all of the fluid stored in chamber 130-1 may require: i) a single cycle of sweeping a mechanical pump element 186-1 along the segment 1110, ii) less than a single cycle of sweeping a mechanical pump element 186-1 along the segment 1110, or iii) multiple cycles of sweeping mechanical pump elements along the segment 1110.

Further, if desired, note that the positive displacement pump 184 can be operated in a continuous manner to provide a continuous flow of fluid to the respective recipient 108 even though the controller 140 occasionally or periodically initiates refilling of the chamber 130-1 during the continuous flow and movement of the mechanical pump elements 186. Alternatively, if desired, the controller 140 can be configured to discontinue operation of the positive displacement pump 184 during a condition in which the chamber 130-1 is refilled with fluid from fluid source 120-1.

In accordance with further embodiments, the controller 140 can be configured to stop (halt) movement of the positive displacement pump 184 and corresponding one or more pump elements (such as peristaltic pump elements) in contact with the segment 1110. While the pump element is stopped, the controller 140 temporarily adjusts the pressure applied to the chamber of the diaphragm pump to measure a respective portion of fluid remaining in the diaphragm pump in a manner as previously discussed. Thus, if desired, embodiments herein can include pausing the positive displacement pumping mechanism to discontinue flow of fluid from the positive displacement pump 184 to the recipient 108 during instances when the amount of fluid remaining in the chamber 130-1 is being measured in a respective sample window.

Figure 6:
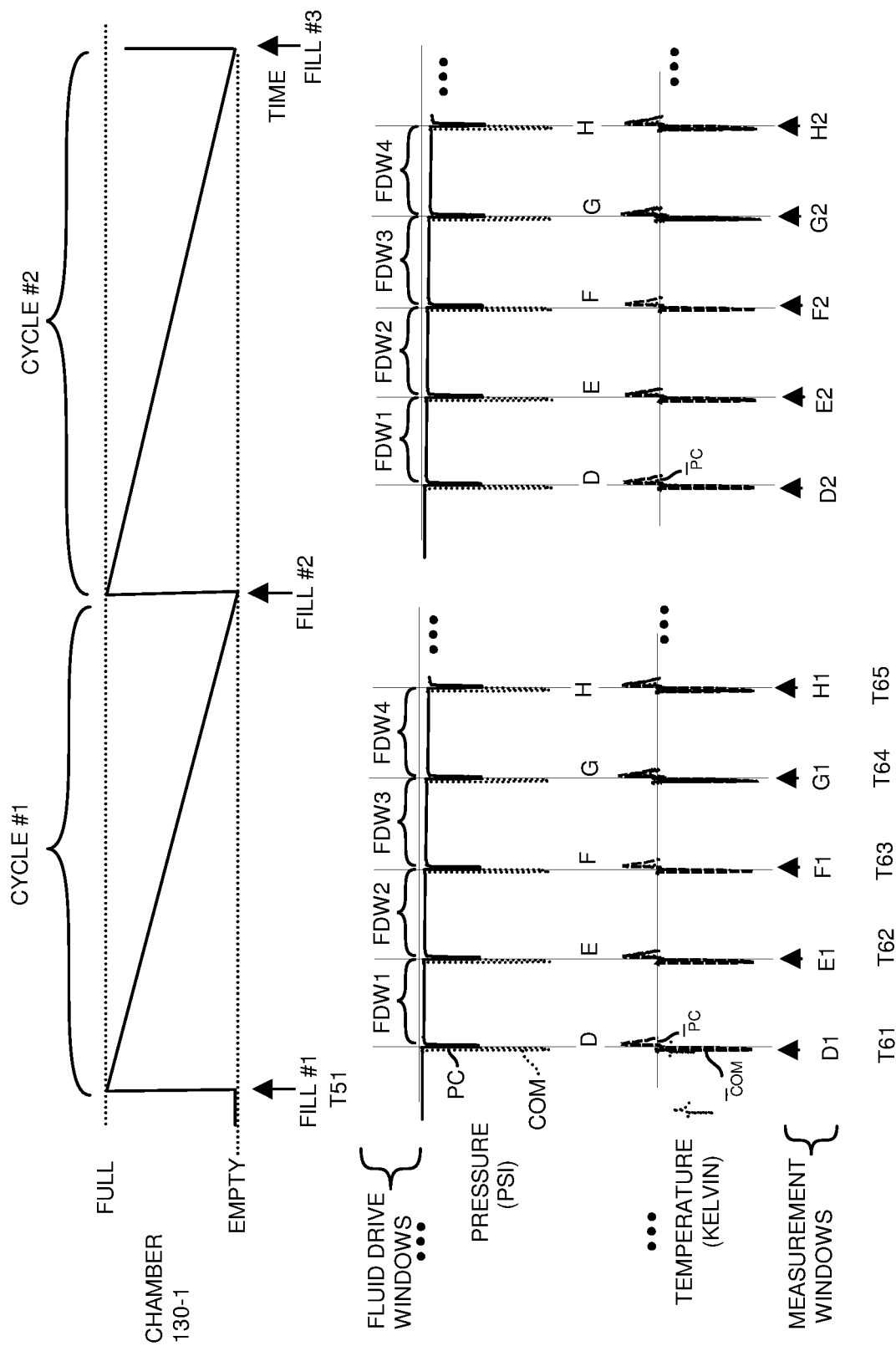
FIG. 6 is an example timing diagram illustrating timing windows associated with multiple pump cycles and multiple measurement windows within each cycle according to embodiments herein.

FIG. 6 is an example timing diagram illustrating multiple measurement windows within each pump cycle according to embodiments herein.

In accordance with embodiments herein, during FILL #1 at time T51, in a manner as previously discussed, the controller 140 applies negative pressure to the chamber 130-2 and chamber 130-1 while valve 125-3 is open, and while mechanical pump element 186-1 obstructs fluid flow and prevents backflow of fluid in segment 1110 to chamber 130-1. During FILL #2, a next successive time of filling chamber 130-1, the controller 140 applies negative pressure again to the chamber 130-2 while valve V8 is open, and while mechanical pump element 186-1 prevents backflow of fluid in segment 1110 to chamber 130-1.

At each of multiple measurement times between a first time of filling FILL #1 and next filling FILL #2, to measure fluid in the chamber 130-1 of the diaphragm pump 130, the controller 140 temporarily adjusts application and a magnitude of the applied positive pressure to chamber 130-2 in between windows (fluid drive windows FDW1, FDW2, FDW3, FDW4, etc.), which occur between fill times FILL #1 and FILL #2.

Interrupting application of pressure to chamber 130-2 (while valve 125-3 controlled by signal V8 is closed) can include temporarily changing the gas pressure from chamber 130-2 at each of multiple windows D1, E1, F1, G1, H1, etc.) to measure an amount of fluid remaining in chamber 130-1 at respective times T61, T62, T63, T64, T65, etc.

The controller 140 uses the measured amount of fluid in the chamber 130-1 at multiple sample times to derive a rate of delivering the fluid from the chamber 130-1 downstream to the segment 1110. For example, the chamber may hold 0.5 ml (milliliters) of fluid following FILL #1. Assume that measurement in window D1 around time T61 indicates 0.5 ml in the chamber; measurement in window D2 around time T62 indicates 0.4 ml in the chamber; measurement in window D3 around time T63 indicates 0.3 ml in the chamber; measurement in window D4 around time T64 indicates 0.2 ml in the chamber; and so on. If the measurement windows are spaced apart by 4 seconds, then the controller 140 determines the rate of flow through the diaphragm pump 184 to be 0.3 ml/12 Seconds=90 milliliters per hour.

In accordance with more specific embodiments, the controller 140 further controls the positive displacement pump 184 and mechanical pump element 186-1 in contact with the segment 1110 of fluid conduit to continuously move along a length of the segment 1110 (such as even during FILL #1, FILL #2, etc.) to provide corresponding continuous flow of fluid from the segment 1110 to the recipient 108 in a respective delivery window.

As previously discussed, during each of multiple measurement windows (D1, E1, F1, G1, H1, for cycle #1, D2, E2, F2, G2, H2, for cycle #2, etc.) of interrupting application of the pressure within the delivery window, the controller 140 measures a respective portion of fluid remaining in the diaphragm pump 130. Note again that details of measuring the amount of fluid in chamber 130-1 are discussed above in FIG. 10A as well as elsewhere throughout this specification.

The controller 140 utilizes the respective measured portions of fluid remaining in the diaphragm pump 130 as measured during the multiple measurement windows (D1, E1, F1, G1, H1, for cycle #1, D2, E2, F2, G2, H2, for cycle #2, etc.) to calculate a rate of fluid delivered by the positive displacement pump 184 to the recipient 108. In the above example, as previously discussed, the controller 140 determines the rate of flow through the diaphragm pump 184 to be 0.3 ml/12 Seconds=90 milliliters per hour. This indicates that the rate of fluid delivered by the positive displacement pump 184 is 90 milliliters per hour. Accordingly, the controller 140 utilizes the respective measured portions of fluid remaining in the chamber 130-1 of the diaphragm pump 130 as measured during the multiple measurement windows to calculate a rate of fluid delivered by the positive displacement pump 184 to the recipient 108.

As further discussed below, the controller 140 can be configured to use the measured flow rate to control operation of the positive displacement pump 184 such that the positive displacement pump 184 delivers fluid to the recipient at a desired rate. For example, as further discussed below, if the flow rate of delivering fluids as indicated by measurements of the chamber 130-1 over time is less than a desired rate, the controller 140 increases a rate of the positive displacement pump 184 delivering fluid to the recipient. In one embodiment, the controller 140 increases a rate of moving the mechanical pump element 186-1 along segment 1110 to increase the rate of fluid flow to recipient 108. Conversely, if the flow rate of delivering fluids as indicated by measurements of the chamber 130-1 over time is greater than a desired rate, the controller 140 decreases a rate of the positive displacement pump 184 delivering fluid to the recipient 108. In one embodiment, the controller 140 reduces a rate of moving the mechanical pump element 186-1 along segment 1110 to decrease the rate of fluid flow to recipient 108.

Figure 7:
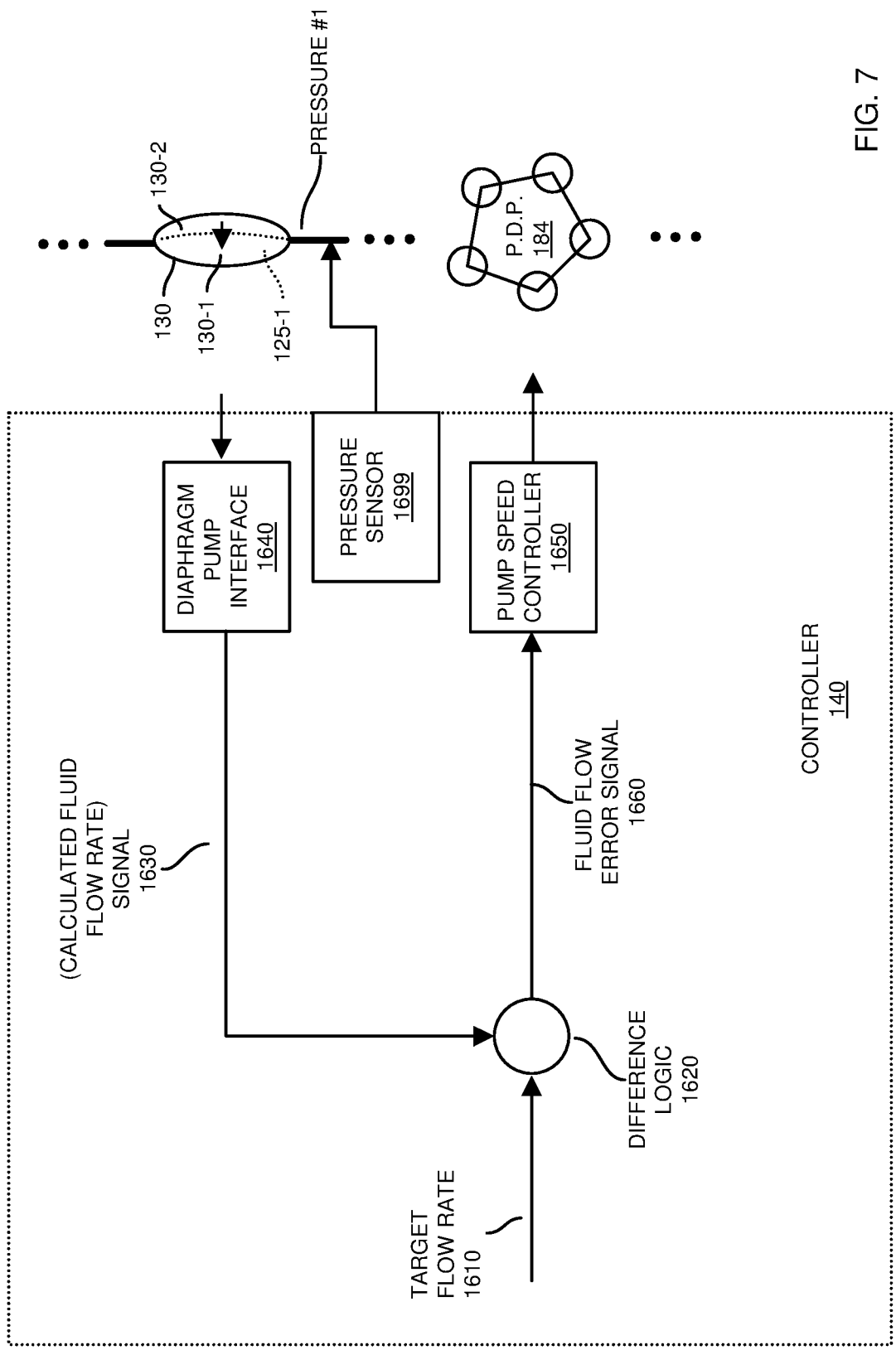
FIG. 7 is an example diagram illustrating control of a respective positive displacement pump based upon a calculated fluid flow rate of fluid delivered by a respective diaphragm pump according to embodiments herein.

FIG. 7 is an example diagram illustrating control of a respective positive displacement pump based upon a calculated fluid flow rate of fluid delivered by a respective diaphragm pump according to embodiments herein.

As previously discussed, to provide precise fluid flow control over a large possible range, the controller 140 measures a flow rate of fluid delivered to the recipient 108 based upon measurements of a respective remaining portion of fluid in the chamber 130-1 over each of multiple sample times (such as measurement windows D1, E1, F1, G1, H1, for cycle #1; measurement windows D2, E2, F2, G2, H2, for cycle #2, etc.).

In one embodiment, as shown, the controller 140 includes diaphragm pump interface 1640. In a manner as previously discussed (such as using multiple measurement windows within a time window), the diaphragm pump interface 1640 is operable to measure a flow rate of the fluid expelled from the chamber 130-1 of the diaphragm pump 130 downstream to the segment 1110 of the fluid conduit. As mentioned, techniques of measuring the flow rate are discussed in FIGS. 9-15. During operation, the diaphragm pump interface 1640 produces signal 1630 indicating the calculated fluid flow rate from diaphragm pump 130 downstream to the positive displacement pump 184. The flow rate of fluid through the diaphragm pump 130 is generally (with slight variations over time) the same flow rate that the positive displacement pump 184 delivers fluid downstream to the recipient 108.

In accordance with further embodiments, the controller 140 utilizes the measured flow rate of the fluid (as detected from measuring respective remaining portions of fluid in the chamber 130-1 of the diaphragm pump 130 over multiple sample times T61, T62, T63, T64, etc.) to control (adjust) a sweep rate of moving the mechanical pump elements 186 along the segment 1110 of the fluid conduit to provide delivery of fluid from the positive displacement pump (and corresponding elastically deformable conduit) to the recipient 108 as specified by a desired flow rate setting (such as a user selected rate).

For example, the difference logic 1620 produces a respective flow error signal 1660 indicating a difference between the calculated fluid flow rate as indicated by signal 1630 (as measured from the diaphragm pump 130) and the target flow rate 1610.

If the measurement of fluid flowing through the diaphragm pump 130 (as measured over time) is greater than the desired flow rate setting, resulting in a positive flow error signal 1660, the positive displacement pump speed controller 1650 of the controller 140 decreases a current rate of the positive displacement pump 184 delivering fluid by reducing a rate of sweeping the mechanical pump element 186-1 along segment 1110. Conversely, if the measurement of the fluid flowing through the diaphragm pump 130 as detected by the controller 140 is less than the desired flow rate setting, resulting in a negative flow error signal 1660, the pump speed controller 1650 of controller 140 increases the rate of the positive displacement pump 184 delivering fluid to the recipient by increasing a rate of sweeping the mechanical pump element 186-1.

In this manner, the controller 140 uses the flow error signal 1660 to control the fluid flow to the target flow rate 1610. Accordingly, in one embodiment, the measured rate of fluid flow through the diaphragm pump 130 can be used as a basis to control the downstream peristaltic pump 184 to provide very accurate fluid flow over a large range.

As further example, between time T61 and time T64, assume that the controller 140 is controlling the mechanical pump element 186-1 to move along segment 1110 at a linear rate of 2.0 millimeters per second, which resulted in a flow rate of 90 milliliters per hour as indicated above. If the target flow rate is 108 milliliters per hour, the error signal 1660 indicates—18 milliliters per hour. To deliver fluid at an appropriate rate of 108 milliliters per hour, the controller 140 increases a rate of moving the mechanical pump element 186-1 to a rate of 2.4 millimeters per second along segment 1110.

As previously discussed, the unique fluid delivery apparatus including a diaphragm pump 130 (to measure a fluid delivery rate) and a positive displacement pump 184 (to control physical pumping of fluid to a recipient 108) provides advantageous delivery of fluid in comparison to conventional techniques. For example, the fluid delivery apparatus and corresponding methods as described herein provide one or more of the following advantages over conventional techniques: i) fast start and stop time to reach desired delivery flow rate set point, ii) large dynamic range to control flow rates from 0.1 milliliters per hour or lower to 1200 milliliters per hour or higher, iii) flow rate control that is immune to inlet or outlet pressure changes, iv) flow rate control that is immune to large variations in fluid properties (such as viscosity), and so on.

Additionally, application of positive pressure to the diaphragm pump as discussed herein feeds fluid to a positive displacement pump, resulting in better flow continuity. Additionally, the diaphragm pump is operable to draw fluid using negative pressure. In such an instance, the diaphragm pump can draw fluid from a container source disposed lower in elevation than the diaphragm pump.

Figure 8:
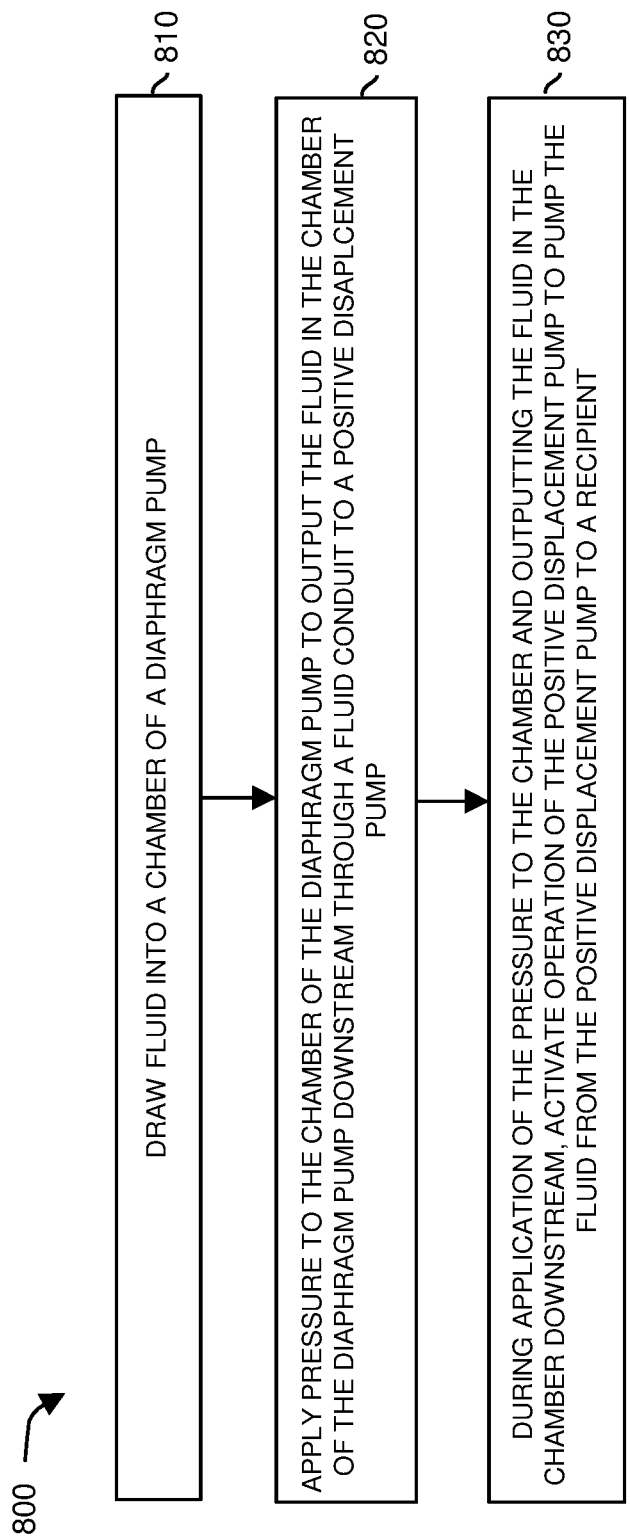
FIG. 8 is an example diagram illustrating a method of delivering fluid to a respective recipient using a combination of a diaphragm pump and a positive displacement pump according to embodiments herein.

FIG. 8 is an example diagram illustrating a method of delivering fluid to a respective recipient using a combination of a diaphragm pump and a peristaltic pump according to embodiments herein.

In processing operation 810 of flowchart 800, the controller 140 (hardware and/or executed instructions of software) draws fluid from fluid source 120-1 into chamber 130-1 of the diaphragm pump 130.

In processing operation 820, the controller 140 applies pressure to the chamber 130-1 of the diaphragm pump 130 to output the fluid in the chamber 130-1 of the diaphragm pump 130 downstream through a fluid conduit to positive displacement pump 184.

In processing operation 830, during application of the pressure to fluid in the chamber 130-1 and outputting the fluid from the chamber downstream to the positive displacement pump 84, the controller 140 activates operation of the positive displacement pump 184 to pump the fluid from the positive displacement pump 184 to a recipient 108.

Control System:

In one embodiment, using a known reference volume C1 (chamber 150), the volume of an unknown volume C2 (pump chamber 130-2) can be measured using the Ideal Gas Law:

$$PV = nRT$$

Where:
P=Pressure
V=Volume
n=number of molecules
R=the gas constant
T=Temperature The basic fluid flow measurement involves calculating the instantaneous volume of C2 at multiple points in time. The change in volume over time is the average flow rate over that time:

$$Q = \frac{C2_{t0} - C2_{t1}}{t_1 - t_0}$$

Where:
Q=Flow rate
t=the time the respective volume measurements are taken
C2=the volume of pump chamber 130-2

The volume measurement utilizes the known volume of C1 (Chamber 150) and the isolation valve 160-5. The volume measurement cycle is as follows:

1. Fluid valves 125-3 and 125-2 (optional) are closed, halting fluid flow into or out of the chamber and temporarily holding the volume of chamber 130-1 constant. As a result, the air volume in chamber 130-2 (C2) is also constant during the measurement.
2. Air valve 160-5 is closed isolating chamber 130-2 (C2) and chamber 150 (C1). Additionally, valves 160-4 and 160-1 are also closed further isolating the chambers.
3. Air Valve 160-3 is opened venting chamber 150 to atmospheric pressure.
4. Air Valve 160-3 is closed again isolating Chamber 150.
5. At this point in time the pressure reading of sensor 135-5 is recorded (P2) and the pressure reading of the sensor 135-3 is recorded (P1). These two pressure values are shown at time t1 on Graph 610.
6. Next valve 160-5 is opened connecting chamber 130-2 (C2) and chamber 150 (C1).
7. At this point in time shown as time t2 on Graph 610 the merged pressure (Pmerge) is recorded by pressure sensors 135-5 and 135-3. Since the chambers are now connected the pressure by each of the sensors 135-5 and 135-3 is the same.

The pressure measurements recorded during this cycles are used in the following equations to calculate the unknown volume of chamber 130-2 (C2):
P1=pressure of chamber 150 (C2)
P2=pressure of chamber 130-2 (C1)
V1=volume of chamber 150 (C2)
V2=volume of chamber 130-2 (C1)
T1=temperature of chamber 150 (C2)
T2=temperature of chamber 130-2 (C1)

For chamber 150 (C2):

$$\frac{P1V1}{RT1} = n1$$

For chamber 130-2 (C1):

$$\frac{P2V2}{RT2} = n2$$

At time t1 when the chambers are isolated:

$$\frac{P1V1}{RT1} + \frac{P2V2}{RT2} = n1 + n2 = n12$$

As previously stated, the volume of chamber 130-2 (C2) denoted by V2 is unknown. To measure V2, the chambers are connected via valve 160-5, and molecules of gas are transferred from one chamber to the other.

At time t2 when the chambers are connected and pressures are the same:

$$\frac{PmV1}{RT1} + \frac{PmV2}{RT1} = n12$$

Where Pm in this case is the merged pressure of the combined chambers and the pressure readings of P1 and P2 are substantially equivalent. Since mass is conserved and the total number of molecules of gas in both chambers does not change during this measurement cycle the equations can be written as:

$$\frac{PmV1}{RT3} + \frac{PmV2}{RT4} = \frac{P1V1}{RT1} + \frac{P2V2}{RT2}$$

At this point it is common to simplify the equations by utilizing Boyle's law and assuming that the temperature of the system is constant during the measurement cycle. With this assumption the equations reduce to:

$$PmV1 + PmV2 = P1V1 + P2V2$$

Solving for the unknown volume (V2) of chamber 130-2 (C2) the equation can be rewritten as:

$$V2 = V1 \frac{(P1 - Pm)}{(Pm - P2)}$$

Assuming that the system is at a constant temperature greatly simplifies the equations but as previously described, system dynamics can cause transient temperature changes that can result in erroneous pressure readings which can cause volume calculation errors. If faster measurement speed or improved accuracy are required, then the assumption of constant temperature may not be appropriate. If desired, estimated temperature can be used to provide more accurate flow measurement readings as further discussed below.

Due to the fact that the gas has very low mass it is difficult if not impossible to measure gas temperature quickly and accurately using readily available temperature sensor technologies such as thermocouples, RTD, etc. The only practical way to improve volume calculation accuracy using temperature is to estimate temperature changes in the gas using knowledge of the system states and the dynamic changes induced by manipulation of the control valves 160-1 to 5 and fluid valves 125-3,2.

Measurement Algorithm Implementing Discontinuous Fluid Flow and/or Estimated Temperature to Calculate Fluid Flow As an alternative to using conventional techniques to measure a flow of fluid to the recipient 108, by way of a further non-limiting example embodiment, note that the controller 140 can be configured to implement a mass fluid flow-based measurement algorithm to take into account the ideal gas laws and mass conservation. The equations hold for a closed system.

$$M_{a1} + M_{b1} = M_{a2} + M_{b2} \quad \text{(equation 1)}$$

$$PV = MRT \rightarrow M = \frac{PV}{RT} \quad \text{(equation 2)}$$

R is a constant, so the equations factor down to:

$$\frac{P_{a1}}{T_{a1}} V_a + \frac{P_{b1}}{T_{b1}} V_b = \frac{P_{a2}}{T_{a2}} V_a + \frac{P_{b2}}{T_{b2}} V_b \quad \text{(equation 3)}$$

Estimation of temperatures as disclosed herein enables quick fluid flow measurements and allows the fluid delivery system 100 (device, hardware, etc.) and controller 140 to operate without stopping the fluid flow during fluid flow measurements by taking into account the full system states (such as temperature), rather than assuming that the system states remain constant through the cycle.

More specifically, in one embodiment, an appropriate drive pressure can be applied to a drive chamber side (such as chamber 130-2) of a diaphragm pump 130 to deliver fluid in a fluid chamber side (chamber 130-1) of the diaphragm pump 130 to a target recipient 108. Further embodiments herein can include temporarily modifying a magnitude of gas pressure applied to the chamber 130-2 at one or more times during a delivery cycle to perform a volume check to identify how much of the fluid is present in the fluid chamber 130-1 of the diaphragm pump 130 over time.

In one embodiment, the flow rate of fluid pumped to a target recipient equals the change in volume of fluid in the chamber 130-2 of diaphragm pump 130 over time.

During times of modifying application of pressure to the chamber 130-2, embodiments herein can include taking into account estimated changes in temperature of the gases resulting from adiabatic heating and cooling due to rapid pressure changes in one or more chambers when calculating the flow rate of the fluid through the diaphragm pump 130 downstream to the positive displacement pump 184.

In one embodiment, a mass balance measurement is dependent on the temperature of the working fluid. Given required measurement speed noted above, the gas experiences adiabatic heating and cooling during the measurement cycle. It is impractical, if not impossible, to measure (with a temperature sensor) the gas temperature directly in the time frame needed; therefore a thermal estimator is used to predict the gas temperature. In other words, the temperature of gases in one or more volumes as discussed herein can change so quickly that a physical temperature sensor is unable to detect a respective change in temperature.

FIG. 9 is an 1 example diagram illustrating gas temperatures in different resources during a delivery cycle according to embodiments herein. As described herein, one or more temperatures can be estimated based on known system information as discussed in more detail below.

Another requirement of infusion systems may be to maintain continuous flow. In one embodiment, the fluid delivery system as discussed herein does not stop the pumping (such as pumping fluid via positive displacement pump 184) during a flow rate measurement. Thus, embodiments herein can include providing a continuous or substantially continuous flow of fluid delivery to a respective target recipient.

In order not to introduce measurement error, the volume measurement cycle can be performed extremely fast such as on the order of milliseconds. According to embodiments herein, a measurement cycle can be less than 200 milliseconds. The fill cycle, such as filling the chamber of the diaphragm pump with fluid, also can be performed very fast to minimize flow variation.

When the gases are moved at this high speed for all of the reasons above the isothermal assumption typically used to simplify the Ideal Gas Law and Boyle's Law becomes invalid.

Specifically, the assumption that the gas is at one constant temperature during the measurement cycle is no longer true.

It is observed that the gas experiences adiabatic heating and cooling during the measurement cycle. As previously discussed, embodiments herein include estimating gas temperatures to compensate for these errors.

In order to account for the temperature effects due to adiabatic heating and cooling of the gas the pressure and volume relationships yield:

$$V_{pc} = V_{com} \frac{\left(\frac{P_{com2}}{T_{com2}} - \frac{P_{com1}}{T_{com1}}\right)}{\left(\frac{P_{pc1}}{T_{pc1}} - \frac{P_{pc2}}{T_{pc2}}\right)} \quad \text{(equation 4)}$$

By way of a non-limiting example, the temperature can be estimated by tracking the system state variables at each time step of the control loop. The physical parameters of the delivery system, such as volume, fluid conduit size (in which the fluid is air), and heat transfer coefficients combined with the measured pressures allow the system to calculate an estimated temperature in each of the gas volumes at any point during the pumping cycle using the following energy balance equation:

$$\frac{dT_i}{dt} = \frac{1}{M_i C_v} \left[ C_p \sum_j T_j Q_{ji} - C_p T_i Q_{out} - C_v T_i - (Q_{in} - Q_{out}) + H(T_{wall} - T_i) \right] - \left(\frac{C_p}{C_v} - 1\right) \cdot \frac{T_i}{V_i} \frac{dV_i}{dt} \quad \text{(equation 5)}$$

Where:

V=volume

Cv=specific heat at constant volume

Cp=specific heat at constant pressure

T=temperature
Q=mass flow
H=heat transfer coefficient

More Detailed Description of Embodiments

In one non-limiting example embodiment, the fluid pumping system as described herein is centered around a pneumatically driven diaphragm (such as diaphragm pump 130), Intermediate Pumping Chamber ("IPC") that consists of a volume bifurcated by a flexible diaphragm (membrane 127). One side of the IPC is connected to the pneumatic portion of the fluidic system. The other side of the IPC is connected to the hydraulic portion of the fluidic system. As previously discussed, hydraulic pumping is achieved by applying alternating positive and negative pressure to the pneumatic side (chamber 130-2) of the IPC, thus moving the diaphragm (membrane 127) back and forth (or in and out).

Referring again to FIG. 2, as previously discussed, the controller 140 of the fluid delivery system 100 controls operation of diaphragm pump 130 in disposable cassette 104 to precisely deliver fluid from one or more fluid sources such as fluid source 120-1 downstream positive displacement pump 184, which in turn, pumps fluid to a respective recipient 108.

In one embodiment, the flow of liquid through the system is controlled by adjustments to the drive pressure from the positive tank 170-1. In this example embodiment, flow rate is measured using periodic volume calculations described below, and the control parameters are adjusted accordingly to drive the error between measured flow rate and target flow rate to zero.

Pump Cycle Overview

In the following embodiment, note that a pump cycle is defined as a motion of drawing fluid from fluid source 120-1 into a diaphragm pump 130 and then applying pressure to the diaphragm pump 130 to deliver the fluid downstream to the segment 1110 of positive displacement pump 184. In accordance with a specific non-limiting example embodiment, a pump cycle can be defined as at least partially moving of the membrane 127 in the diaphragm pump 130 from one extreme (such as "full") to another extreme (such as "empty").

As shown in FIG. 2, and more specifically in FIG. 3, membrane 127 divides the diaphragm pump 130 to include chamber 130-1 and chamber 130-2. Membrane 127 prevents fluid in chamber 130-1 from passing to chamber 130-2, and vice versa.

The membrane 127 dividing diaphragm pump 130 into chamber 130-1 and chamber 130-2 is flexible (elastically deformable). When a negative (gas) pressure is applied to chamber 130-2, the volume of chamber 130-1 expands, drawing fluid from fluid source 120-1 through open valve 125-3 into chamber 130-1.

Conversely, when a positive pressure is applied to chamber 130-2 (while the valve 125-3 is closed and optional valve 125-2 is opened), the volume of chamber 130-1 decreases, expelling fluid from chamber 130-1 downstream to the positive displacement pump 184.

Note again that positive displacement pump 184 can be any suitable type of pump device.

The total volume or capacity of chamber 130-1 and chamber 130-2 is substantially constant regardless of the position of the membrane 127. Based on knowing the volume of fluid in chamber 130-2, one is able to determine a corresponding volume of chamber 130-1. For example, if the total volume of the diaphragm pump 130 is Vtotal, and the volume of chamber 130-2 is V2, the fluid delivery system 100 generally can determine the volume of chamber 130-1 by subtracting V2 from Vtotal.

In this example embodiment, as shown in FIG. 2, temperature sensor 152 measures a temperature (e.g., Tct) of chamber 150 (common tank) and provides a baseline from which to estimate the temperatures of gases in one or more of the following resources: chamber 150, pump chamber 130-2, positive tank 170-1, negative tank 170-2, etc.

As further discussed below, estimation of the temperature enables a more accurate assessment of how much of fluid in pump chamber 130-1 has been pumped in a direction towards the target recipient 108 over conduit path 138 (such as a path from diaphragm pump 130 through a combination of valve 125-2 (optional), fluid conduit segment 1110, gas detection resource 110, to recipient 108).

Initially, to fill the chamber 130-1 with fluid from fluid source 120-1, the controller 140 of fluid delivery system 100 applies a negative pressure or vacuum to chamber 130-2 (while valve 125-2 is closed and/or positive displacement pump 184 obstructs the segment 1110 from fluid flowing backwards to diaphragm pump 130). At such time, pump chamber 130-2 reduces in volume, causing the chamber 130-1 to fill with fluid received from fluid source 120-1 through open valve 125-3 (such as an active valve controlled by control input V8 from controller 140).

Assume that prior to filling, the chamber 130-1 is substantially empty of fluid. In one embodiment, to draw fluid into chamber 130-1 with negative pressure from tank 170-2 as discussed above, the controller 140-1 generates respective control signals V1, V5, and V8 to open corresponding valve 160-1, 160-5, and valve 125-3 (while all other valves are closed) to draw fluid from fluid source 120-1 through open valve 125-3 into chamber 130-1.

Subsequent to chamber 130-1 being filled with fluid, the controller 140 controls settings of the valves 160 to apply a positive pressure from tank 170-1 to chamber 130-2 of diaphragm pump 130. For example, via generation of control signals V4, V5, and V9, the controller 140 opens valves 160-4, 160-5, and valve 125-2 and closes all other valves. The flow of gas from positive tank 170-1 to pump chamber 130-2 causes pumping of fluid from chamber 130-1 through valve 125-2 along fluid conduit to the positive displacement pump 184 and corresponding segment 1110. As previously discussed, during application of positive pressure to chamber 130-2, closing of valve 125-3 prevents fluid in chamber 130-1 from flowing back into fluid source 120-1.

Note that conduit path 138 also can include gas detector resource 110. The gas detector resource 110 can be configured to detect presence of air (or other gases) in the fluid being pumped through conduit path 138 to the target recipient 108. Based on feedback from the gas detector resource 110 as monitored by the controller 140, the controller 140 can be configured to stop flow and sound an alarm in the event of detecting presence of gas in the fluid pumped to the target recipient 108.

As previously discussed, during a delivery phase, the controller 140 can be configured to mainly apply pressure to chamber 130-2 with gas from tank 170-1 or tank 150 to cause the fluid in chamber 130-1 to flow downstream to positive displacement pump 184. Delivery of the fluid from the positive displacement pump 184 through the conduit path 138 to target recipient 108 can be controlled by the controller 140 in accordance with a pre-selected fluid delivery rate as discussed herein (see an example in FIG. 7). As further discussed below, embodiments herein can include at least temporarily discontinuing application of pressure to chamber 130-2 (in each of multiple measurement windows) in order to perform respective measurements of fluid remaining in chamber 130-1. As shown and discussed, adjusting application of pressure to the chamber 130-2 in a manner as discussed herein temporarily reduces or stops a flow of fluid from the chamber 130-1 to positive displacement pump 184 for the benefit of measuring prior fluid flow downstream from the diaphragm pump 130 to the positive displacement pump 184.

During a fluid delivery phase, the controller 140 supplies a substantially constant pressure to the chamber 130-2. Because the membrane 127 is flexible, the pressure in chamber 130-2 exerts a force on the fluid in chamber 130-1. In general, via application of the appropriate pressure to chamber 130-2, the controller 140 is able to feed fluid at a substantially constant rate downstream (although occasionally interrupted) to the positive displacement pump 184. Note that the delivery system 100 can be perturbed, resulting in errors in the flow rate. For example, as previously mentioned, the fluid source 120-1 may be squeezed, the elevation of fluid source 120-1 may change, etc. Any of these conditions can impact an accuracy of a desired fluid delivery rate.

Note that in addition to applying positive pressure to the pump chamber 130-2 during a fluid delivery phase, embodiments herein can include occasionally checking how much of the fluid drawn into the chamber 130-1 has been pumped towards the target recipient 108 through the fluid conduit path. This enables the controller 140 to accurately determine the actual flow rate of fluid, even during times when the system conditions are perturbed.

More specifically, one way to measure a fluid delivery rate during a respective delivery phase is to repeatedly measure how much of the fluid in the chamber 130-1 has been pumped towards target recipient 108 on conduit path 138 at one or more MEASUREMENT times during the delivery phase. For example, the controller 140 can initiate checking the volume of gas in chamber 130-2 over multiple sample times of a positive pressure delivery cycle. Because it is known how much gas is initially in the chamber 130-2 at the beginning of a delivery phase, and based on calculating how much gas is in chamber 130-2 at different times, etc., the controller is able to accurately measure a rate of pumping or delivering the fluid from fluid source 120-1 over conduit path 138 to the target recipient 108 in between times of filling the chamber 130-2. Thus, the controller 140 is able to accurately measure fluid delivery in very small increments of time between successive cycles of refilling the chamber 130-1 with additional fluid.

One embodiment herein includes calculating how much fluid remains in chamber 130-1 based on knowing the volume of chamber 130-2. That is, the volume of the chamber 130-1 can be calculated by subtracting the volume of chamber 130-1 from the (known) total capacity of both chambers in the diaphragm pump 130. As discussed below, the volume of chamber 130-2 is initially an unknown quantity but is calculated based on pressure and estimated temperature.

FIG. 10A is an example diagram illustrating fluid measurements during fluid delivery according to embodiments herein. As shown, graph 510-1 illustrates application of pressure for more than 95% of a delivery cycle. The signal PC represents the pressure of gas in chamber 130-2; the signal COM represents the pressure of gas in the chamber 150.

In between times of applying pressure to chamber 130-2 (such as times labeled as FLUID DELIVERY), the controller 140 of fluid delivery system 100 periodically or occasionally, at multiple times, performs a measurement (labeled as MEASUREMENT) to determine a volume of fluid left in chamber 130-2 of diaphragm pump 130. By way of non-limiting example embodiment, the controller 140 initiates applying an approximately constant pressure during FLUID DELIVERY portions of a fluid delivery cycle while the applied pressure to chamber 130-2 is reduced briefly, as previously discussed, during each respective MEASUREMENT window D, E, F, etc.

In this example embodiment, graph 520-1 illustrates changes in temperature of respective gases that occur during each of the measurements. For example, signal Tcom represents the estimated temperature of the gas in the chamber 150; signal Tpc represents the temperature of gas in the chamber 130-2.

In general, in one non-limiting example embodiment, the duty cycle of performing measurements versus delivering fluid is relatively small. That is, in one non-limiting example embodiment, most of a fluid delivery cycle (delivery phase) can be used to deliver corresponding fluid in chamber 130-1 of pump 130 to recipient 108. For a small portion of the delivery cycle, during a volume check in chamber 130-1, the controller 140 operates respective resources to perform a corresponding volume MEASUREMENT of the chamber 130-2 as shown. Recall that after a volume of the chamber 130-2 is known, the volume of chamber 130-1 can easily be determined because total possible capacity of chamber 130-1 and chamber 130-2 is known.

FIG. 10B is an example diagram illustrating more particular details of a fluid delivery cycle according to embodiments herein.

Graph 510-2 shows the pressures measured in the system during a fluid delivery cycle. Graph 520-2 shows the estimated temperatures measured in the system during a fluid delivery cycle.

At or around time [A] in FIG. 10B, a delivery cycle begins by resetting the pressures in the positive tank 170-1 and negative tank 170-2. The controller 140 sets the solenoid valves 160-1, 160-4, 160-5, and 160-3 (via generation of control signals V1, V4, V5, and V3) to a closed position. The controller 140 activates (turns ON) air pump 180 to bring the tanks 170 to the desired operating pressures.

At time [B], while valves 125-2 and 160-3 are closed and valve 125-3 is open, valves 160-1 (V1) and 160-5 (V5) are opened to apply the negative gas pressure in the negative tank 170-2 to the chamber 130-2. As previously discussed, the negative pressure draws the diaphragm membrane 127 back towards tank 150, filling chamber 130-1 with fluid from fluid source 120-1 through valve 125-3. Fluid such as liquid from fluid source 120-1 is drawn into the chamber 130-1 of the diaphragm pump 130. After filling chamber 130-1, the controller 140 closes valve 125-3 and valve 160-1.

At time [C] valves 160-4 (via generation of signal V4) and 160-5 (via generation of signal V5) are opened to apply the pressure in the positive tank 170-1 to the chamber 130-2 of the diaphragm pump 130. This causes the liquid in the chamber 130-2 of the diaphragm pump 130 to flow on conduit path downstream to the positive displacement pump 184 and, eventually, target recipient 108.

In one embodiment, sometime after the chamber 130-2 of diaphragm pump 130 is brought to positive pressure to pump fluid in chamber 130-1 downstream to segment 1110, the controller 140 performs volume calculations such as at times [D], [E], [F], etc. Aspects of the volume calculation are discussed in more detail below. As previously discussed, one or more volume calculations can be performed periodically during the time that the chamber 130-1 is emptying (e.g., during times [C] through [I]).

After the last volume measurement at time [I], or at any time during the delivery phase, the controller 140 calculates a flow rate from the volume measurements. Based on the calculated flow rate the controller 140 can determine if adjustments are needed to the flow control parameter: delivery rate of the positive displacement pump 184 such as peristaltic pump speed.

Note that the fluid delivery cycle restarts when the air pump 180 is turned on at time [J] to reset the pressures in the positive tank 170-1 and negative tank 170-2 again.

Detailed View of a Particular Measure Cycle

FIG. 11 is an example diagram illustrating an example MEASUREMENT cycle (at any of times C through I) during a fluid delivery cycle according to embodiments herein. This is a more specific view of performing a fluid flow rate measurement according to embodiments herein.

Graph 610 illustrates gas pressures in each of multiple volumes. In this example embodiment, the pressure signal labeled PC in graph 610 represents the pressure of a gas in chamber 130-2 as measured by pressure sensor 135-5 (which produces pressure signal P5). The pressure signal labeled COM in graph 610 represents the pressure of a gas in chamber 150 as measured by pressure sensor 135-3 (which produces pressure signal P5).

Graph 620 illustrates estimated temperatures (Tcom and Tpc) of the respective gases in the chamber 150 and chamber 130-2.

At the start of a respective fluid delivery cycle, the chamber 150 (Common Tank or reference chamber), positive tank 170-1, and the diaphragm pump 130 are all at to the same pressure such as the driving pressure of the system. The driving pressure represents the pressure of the gas applied to chamber 130-2 prior to time T1 during which fluid is delivered from diaphragm pump 130 downstream to positive displacement pump 184.

At point [1] in graph 610, the controller 140 generates appropriate control signals to close all of the valves 160 to isolate the gas volumes. The controller 140 controls valve 160-3 (via signal V3) to an open state to vent the chamber 150 (Common Tank) to ambient pressure.

When the pressure in the chamber 150 reaches ambient pressure at approximately point [2], the controller 140 controls valve 160-3 (via generation of signal V3) to a closed position again such that all of the gas volumes are again isolated.

At approximately time T1 (shown as points [3] and [4]) when valves 125-3 and valve 125-2 are closed, the controller 140 controls valve 160-5 (via generation of signal V5) to an open state to merge (quickly equalize) the gas in chamber 130-2 with the gas in chamber 150. As shown, the gas pressure in the chamber 130-2 and tank 150 equalize at or around point [5] in graph 610.

In one embodiment, the volume of chamber 130-2 and chamber 150 are approximately the same.

In this example measurement cycle shown in graph 610, assume that opening of valve 160-5 in a manner as previously discussed causes the pressure in the chamber 130-2 to reduce by approximately 50%. The amount of reduction in pressure applied to chamber 130-2 varies depending on a volume of chamber 130-2 and a volume of chamber 150.

After another brief stabilization period or at point [6]), the controller 140 controls valve 160-4 (via generation of signal V4) to an open state again to connect the chamber 130-2 (IPC) and the chamber 150 via a gas pathway to the positive tank 170-1 to bring all three gas volumes up to the driving pressure again, during which the pressure in the chamber 130-2 causes the chamber 130-1 to pump respective fluid to the target recipient 108. Thus, embodiments herein include at least temporarily stopping or reducing fluid flow by closing the downstream valve 125-2 or pausing the motion of the positive displacement pump 184 in order to obtain pressure measurements at different times.

In one embodiment, the actual volume calculation produced by the controller 140 occurs based on measurements of pressure collected by the controller 140 at or around points [3], [4], and [5].

At substantially time T1 or point [4], the controller 140 receives signal P5 generated by pressure sensor 135-5 to determine the pressure Ppc of the gas applied to chamber 130-2.

At substantially time T1 or point [3], the controller 140 receives signal P3 generated by pressure sensor 135-3 to determine the pressure Pcom of the gas in chamber 150.

At substantially time T2 or point [5], the controller 140 receives signal P3 or P5 generated by pressure sensor 135-3 and/or pressure sensor 135-5 to determine the pressure Pmerge of the gas in chamber 150.

According to one embodiment, the controller 140 determines the volume of gas in chamber 130-2 using ideal gas laws and an assumption that the system is isothermal during the measurement (ignoring temperature changes) as follows:

$$P_1 V_1 = P_2 V_2 \quad \text{(equation 6)}$$

For:
$V_{pc}$=Unknown volume of the chamber 130-2 of diaphragm pump 130 $V_{com}$=the known volume of the chamber 150 (Common Tank)
$P_{pc}$=pressure of the chamber 130-2 at point [4]
$P_{com}$=pressure of the chamber 150 (Common Tank) at point [3]
$P_{merge}=P_{pc}=P_{com}$ pressure when the two chambers (130-2 and 150) are equalized at point [5]

$$V_{pc} P_{pc} + V_{com} P_{com} = V_{pc} P_{merge} + V_{com} P_{merge} \quad \text{(equation 7)}$$

$$\vdots$$

$$V_{pc} = V_{com} \frac{P_{merge} - P_{com}}{P_{pc} - P_{merge}} \quad \text{(equation 8)}$$

An isothermal calculation assumes that the system under consideration remains at a constant temperature during the observation time period. This equalization (and/or stabilization) of gas can take on the order of seconds to occur, depending on the details of the system. If the volume calculation is performed prior to the system returning to thermal equilibrium, the residual temperature differences will introduce errors in the volume calculation, which will in turn cause errors in the resultant flow rate calculation.

In accordance with one embodiment, in order to achieve the range of flow rates required in an infusion pump system, and to minimize errors due to volume changes during the measurement cycle, the current embodiment can be configured to calculate a volume of fluid pumped to the target recipient 108 before the transient thermal effects have equalized. In order to maintain volume calculation accuracy, embodiments herein take into account thermal effects to produce a more accurate fluid delivery rate.

In one embodiment, the temperature changes in the gas happen too fast to be measured by standard thermal sensors.

In other words, thermal sensors may not be able to accurately measure fast changing temperatures of the gases in tank 150, chamber 130-2, etc., during a respective pressure changes shown in graph 600. To address this issue, one embodiment herein includes estimating temperatures of the volumes of interest to calculate an actual fluid delivery rate. As mentioned, in one embodiment, the temperature sensor 152 measures an average temperature of gas in the common tank 150. However, due to its thermal mass, the temperature sensor 152 may not be able to accurately detect quick changes to an actual temperature of gas in chamber 150.

There are a number of parameters that affect the temperature of the gases in the different volumes (e.g., tank 150, chamber 130-2, etc.) over time. For example, thermal changes come primarily from 3 sources in the pneumatic system:

1. Adiabatic heating or cooling due to pressure changes in the chamber
2. Heat transfer between the gas and the chamber wall
3. Volume change due to flow rate out of the IPC chamber One embodiment herein includes modeling the fluid delivery system 100 to accurately estimate the temperature of the chambers of interest. For example, as mentioned, the change in pressure of chambers (such as pump chamber 130-2 and chamber 150) as shown and discussed with respect to FIG. 11 causes the temperature of the pump chamber 130-2 and the common tank 150 to vary. More specifically, between point 1 and point 2 in FIG. 6, the pressure of the common tank 150 drops significantly, causing the temperature of the gas, Tcom, in chamber 150 (common tank) to drop. As previously discussed, the pressure of gas in the respective chambers (e.g., P5, P3, etc.) is continuously and accurately measured using respective pressure sensors 135-5, 135-3, etc.

In one embodiment, a first model is used to estimate temperature changes in the chambers due to adiabatic heating and/or cooling. In other words, any suitable equations can be used to determine a change in the temperature of the gases in the chambers as a result of the pressures changing. Increasing a pressure of a gas causes an increase in temperature; decreasing a pressure of a gas causes a decrease in temperature.

Another parameter affecting the temperature of the gases in the chambers is the thermal characteristics of the chambers themselves and conduits in between. The dark lines in FIG. 2 represent fluid conduits (such as tubes, channels, or the like) interconnecting the different components in fluid delivery system 100. For example, the dark line extending between diaphragm pump 130 and valve 160-5 represents a conduit; the dark line between valve 160-5 in chamber 150 represents a conduit; and so on. Via respective conduits, each of the components (such as valve 125-3, diaphragm pump 130, valve 160-5, etc.) in fluid delivery system 100 are interconnected.

According to embodiments herein, the thermal properties of the chambers (e.g., common tank 150, pump chamber 130-2, etc.) can be characterized and modeled to identify how quickly they sink or source heat when there is a change in temperature caused by a change in pressure. As an example, and as discussed, the reduction in the pressure of a tank can cause the temperature of the gas in the tank to decrease. The temperature of the tank itself may be higher in magnitude than the temperature of the gas, resulting in a flow of heat from the tank or chamber to the gas therein. Thermal flow causes the temperature of the gas in the chamber to eventually become the substantially the same as the temperature in the respective tank over time. Conversely, an increase in pressure of the tank can cause the temperature to increase. The flow of heat from gas to the tank or chamber decreases the temperature of the gas.

One embodiment herein includes estimating the temperature of the gas and taking into account thermal heat flow using a respective thermal model. The thermal model takes into account the transfer of heat from the gas to the respective chamber or tank and/or a transfer of heat from the respective chamber or tank to the gas. The heat transfer will likely vary depending on the type of material used to fabricate the tanks and respective interconnections. Certain material such as metal will be more thermally conductive; material such as plastic will be less thermally conductive.

As discussed above, the changes in the temperature of the gases due to changes in pressure are deterministic and thus can be accurately estimated. However, the flow of energy from tank to gas or from gas to tank will impact the temperature. Embodiments herein include producing a more accurate estimate of temperature by taking into account these flows of energy at different times based on thermal modeling.

Another factor affecting the temperatures of the gases in the chambers is the volume of the pump chamber 130-2 and how quickly it changes over time due to pumping of the fluid in the diaphragm pump chamber to the positive displacement pump 184 and target recipient. For example, if the fluid in the pump chamber 130-2 is pumped at a very slow rate to target recipient 108, then volume change effects are minor or potentially negligible. Conversely, if the fluid in pump chamber 130-1 is pumped at a relatively high rate to the positive displacement pump 184 and target recipient 108, then the volume change effects become more significant. As discussed herein, embodiments herein take into account the volume changes.

In one embodiment, the controller 140 generates the estimation of temperatures at discrete points in time such as between one second and one nanosecond. For each time step (i.e., each discrete time of producing an estimation of temperature) of the control system, the change in temperature due to those three sources is calculated for each pneumatic volume using the measured pressure as an input. The components (e.g., adiabatic effects, heat transfer effects, volume change effects) can be measured individually and/or in combination to produce a respective estimated temperature.

In the following equations subscripts 'i' and T are used to denote each of the pneumatic volumes 130-2, 150, 170-1, 170-2. The subscript 'i' represents the chamber for which the temperature is being estimated; the subscript 'j' represents a chamber connected to the chamber for which temperature is being estimated. For example, when estimating a temperature for the pump chamber 130-2, the subscript 'i' represents the pump chamber 130-2; subscript 'j' represents the common tank 150. When estimating a temperature for the common tank 150, the subscript 'i' represents the common tank 150; subscript 'j' represents the pump chamber 130-2, and so on.

By way of a non-limiting example, the temperature at time (n+1) is then calculated based on that change rate:

$$\frac{dT_n}{dt} = \text{(Heat Transfer Effects)} + \text{(Pressure Change Effects)} + \text{(Volume Change Effects)} \quad \text{(equation 9)}$$

$$T_{n+1} = T_n + dt\frac{dT_n}{dt} \quad \text{(equation 10)}$$

Heat transfer effects are based on the temperature of the gas in the chamber, the temperature of the chamber wall, and the heat transfer coefficient between the two. For example, in one embodiment:

$$\text{Heat Transfer Effects } H(T_{wall} - T_i) \quad \text{(equation 11)}$$

$T_i$=last estimation of temperature for chamber i
H=heat transfer coefficient
$T_{wall}$=ambient temperature $T_{tc}$ as sensed by temperature sensor 152

Pressure change effects are based on the mass flow from one chamber to another due to pressure differential between the two chambers:

$$Q_{ij} = C_{ij} A_{ij} \sqrt{2\rho_i (P_i - P_j)} \quad \text{(equation 12)}$$

$$Q_{in} = \sum_j Q_{ji} \quad \text{(equations 13 and 14)}$$

$$Q_{out} = \sum_j Q_{ij}$$

$$\text{Pressure Change Effects} = \frac{1}{M_i C_v} \quad \text{(equation 15)}$$

$$\left[ C_p \sum_j T_j Q_{ji} - C_p T_i Q_{out} - C_v T_i (Q_{in} - Q_{out}) \right]$$

Where:
$M_i$=mass of gas in chamber i;
$Q_{ij}$ is the mass flow rate from chamber i to chamber j.
$C_{ij}$ is the discharge coefficient of the valve between chamber i and j
$A_{ij}$ is the area of the orifice of the valve between chamber i and j
$\rho_i$ is the density of the gas in chamber i
Cv=specific heat at constant volume
Cp=specific heat at constant pressure Volume change effects are based on any changes in actual volume of the chamber in question. In one embodiment, this effect only applies to chamber 130-2, which can change size due to motion of membrane 127.

$$\text{Volume Change Effects} = \left( \frac{C_p}{C_v} - 1 \right) \cdot \frac{T_i}{V_i} \frac{dV_i}{dt} \quad \text{(equation 16)}$$

Where:
V=volume
Cv=specific heat at constant volume
Cp=specific heat at constant pressure The estimated temperature curves through the pumping and measurement cycles can be seen in FIGS. 10A, 10B, and 11.

In this method the control system has an estimated temperature for each gas chamber that can be used in a modified ideal gas law volume calculation that takes temperature into account:

$$V_{pc} = V_{com} \frac{\left( \frac{P_{com2}}{T_{com2}} - \frac{P_{com1}}{T_{com1}} \right)}{\left( \frac{P_{pc1}}{T_{pc1}} - \frac{P_{pc2}}{T_{pc2}} \right)} \quad \text{(equation 17)}$$

$V_{pc}$=Unknown volume of the chamber 130-2 of diaphragm pump 130 (e.g., Left IPC)
$V_{com}$=the known volume of the chamber 150
$P_{com1}$=pressure P3 from pressure sensor 135-3 of the chamber 150 at point [3]
$P_{com2}$=pressure P3 from pressure sensor 135-3 of the chamber 150 at point [5]
$P_{pc1}$=pressure P5 from pressure sensor 135-5 of the chamber 130-2 at point [4]
$P_{pc2}$=pressure P5 from pressure sensor 135-5 of the chamber 130-2 at point [5]
$T_{com1}$=estimated temperature of the chamber 150 at point [3A]
$T_{com2}$=estimated temperature of the chamber 150 at point [5A1]
$T_{pc1}$=estimated temperature of the chamber 130-2 at point [4A]
$T_{pc2}$=estimated temperature of the chamber 130-2 at point [5A2]

As previously discussed, the volume of the chamber 130-1 can be calculated by subtracting the calculated VPC (e.g., volume of the pumping chamber 130-2) from the total volume of the diaphragm pump 130. The total volume of the diaphragm pump 130 is equal to the volume of chamber 130-1 plus the volume of chamber 130-2 and is a known quantity.

In a further embodiment, the volume of chamber 130-1 is not calculated, and flow rate is calculated by simply taking the difference in volume between subsequent calculations of the volume of chamber 130-2. In other words, the change in volume of pump chamber 130-2 over time is indicative of a pumping flow rate and can be used as a basis to calculate the flow rate. The controller 140 can be configured to precisely determine a respective flow rate of delivering fluid from chamber 130-1 of diaphragm pump 130 based on the multiple measurements taken at times C, D, E, etc., in FIG. 10B.

The flow rate=(change in volume in chamber 130-2)/
(elapsed time between volume measurements).

Using a temperature-corrected volume calculation (based on estimation of gas temperatures as described herein) allows the system to have a measure sequence that happens on the order of 80 milliseconds, rather than on the order of seconds while maintaining calculation accuracy.

Figure 12:
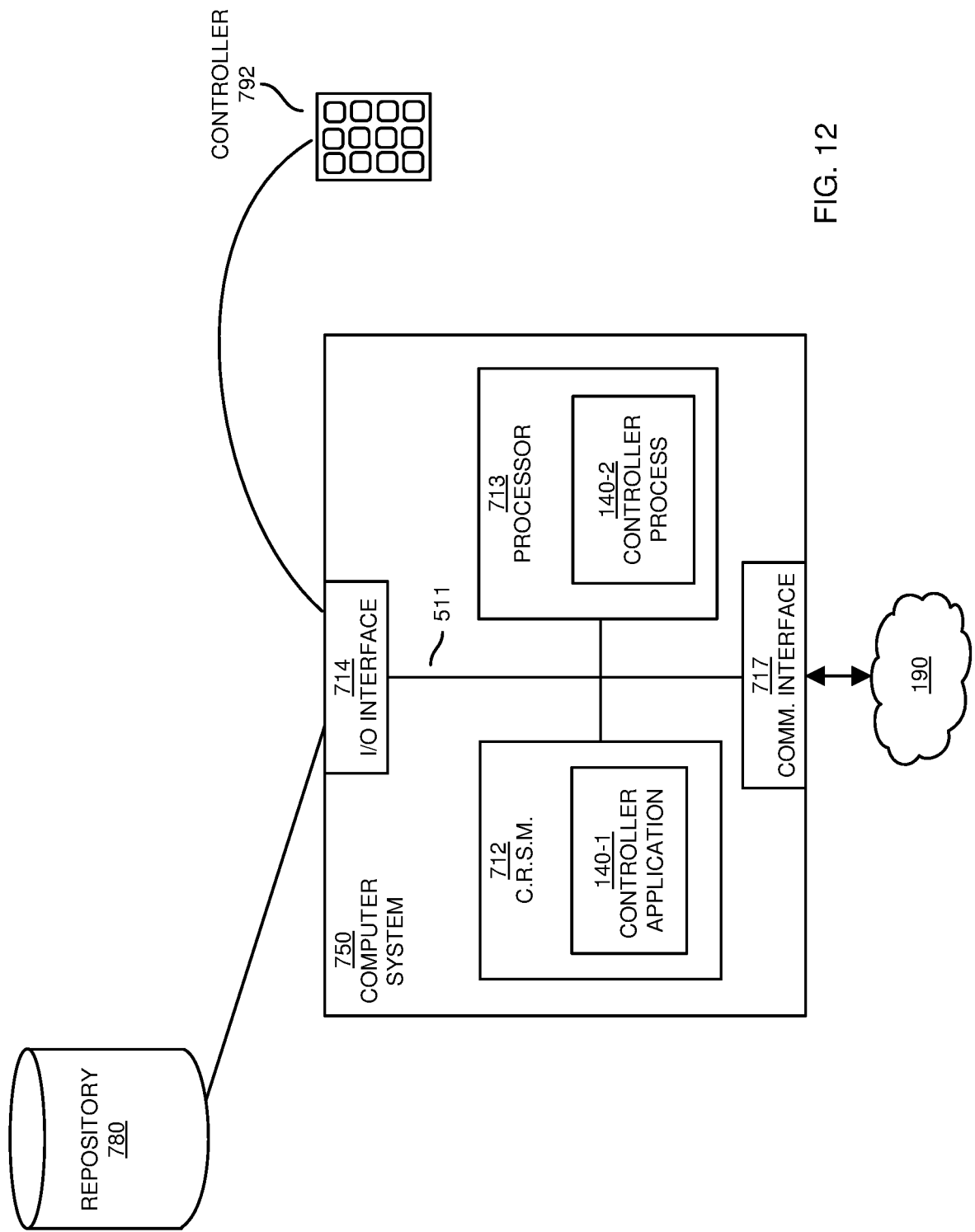
FIG. 12 is a diagram illustrating an example computer architecture in which to execute any of the functionality according to embodiments herein.

FIG. 12 is an example block diagram of a computer device for implementing any of the operations as discussed herein according to embodiments herein.

In one embodiment, fluid delivery system 100 includes a computer system 750 (hardware) to execute controller 140.

As shown, computer system 750 of the present example includes an interconnect 711, a processor 713 (such as one or more processor devices, computer processor hardware, etc.), computer readable storage medium 712 (such as hardware storage to store data), I/O interface 714, and communications interface 717.

Interconnect 711 provides connectivity amongst processor 713, computer readable storage media 712, I/O interface 714, and communication interface 717.

I/O interface 714 provides connectivity to a repository 780 and, if present, other devices such as a playback device, display screen, input resource 792, a computer mouse, etc.

Computer readable storage medium 712 (such as a non-transitory hardware medium) can be any hardware storage resource or device such as memory, optical storage, hard drive, rotating disk, etc. In one embodiment, the computer readable storage medium 712 stores instructions executed by processor 713.

Communications interface 717 enables the computer system 750 and processor 713 to communicate over a resource such as network 190 to retrieve information from remote sources and communicate with other computers. I/O interface 714 enables processor 713 to retrieve stored information from repository 780.

As shown, computer readable storage media 712 is encoded with controller application 140-1 (e.g., software, firmware, etc.) executed by processor 713. Controller application 140-1 can be configured to include instructions to implement any of the operations as discussed herein.

During operation of one embodiment, processor 713 (e.g., computer processor hardware) accesses computer readable storage media 712 via the use of interconnect 711 in order to launch, run, execute, interpret or otherwise perform the instructions in controller application 140-1 stored on computer readable storage medium 712.

Execution of the controller application 140-1 produces processing functionality such as controller process 140-2 in processor 713. In other words, the controller process 140-2 associated with processor 713 represents one or more aspects of executing controller application 140-1 within or upon the processor 713 in the computer system 750.

Those skilled in the art will understand that the computer system 750 can include other processes and/or software and hardware components, such as an operating system that controls allocation and use of hardware resources to execute controller application 140-1.

In accordance with different embodiments, note that computer system may be any of various types of devices, including, but not limited to, a wireless access point, a mobile computer, a personal computer system, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, or in general any type of computing or electronic device. In one non-limiting example embodiment, the computer system 850 resides in fluid delivery system 100. However, note that computer system 850 may reside at any location or can be included in any suitable resource in network environment 100 to implement functionality as discussed herein.

Functionality supported by the different resources will now be discussed via flowcharts in FIGS. 13, 14, and 15. Note that the steps in the flowcharts below can be executed in any suitable order.

Figure 13:
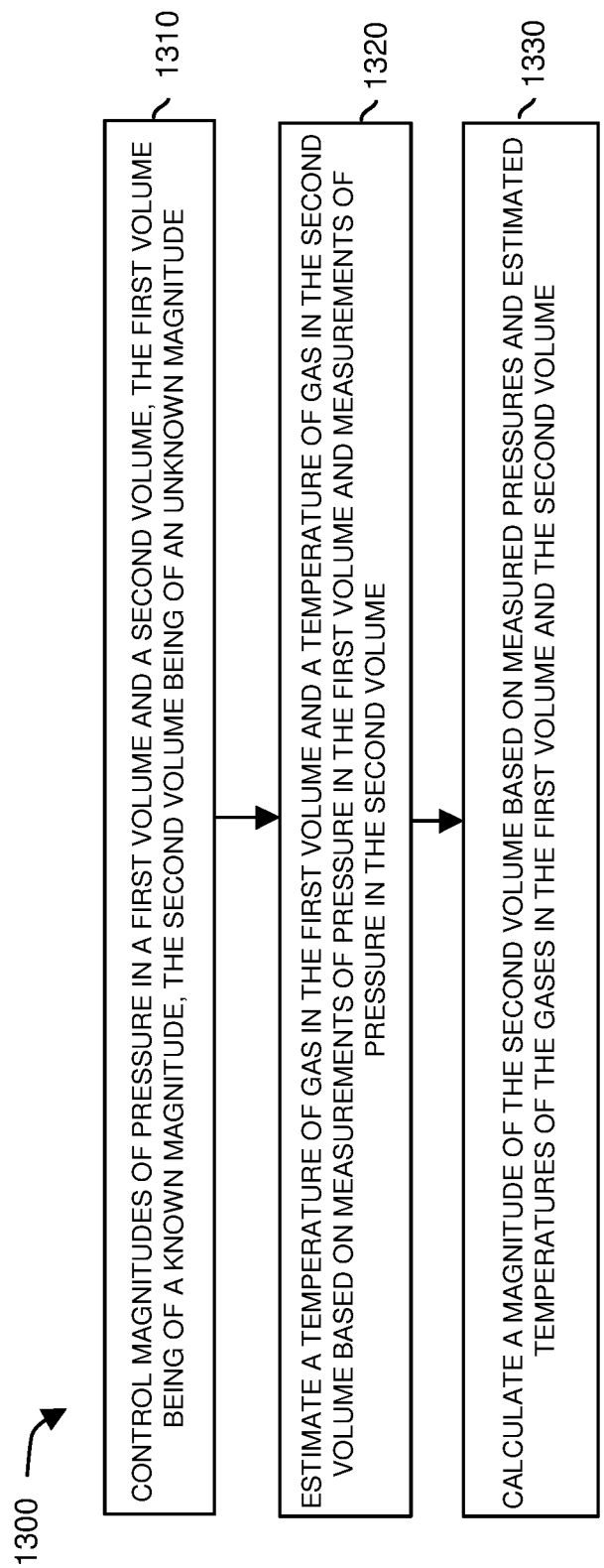
FIGS. 13-15 are example diagrams illustrating methods facilitating flow control measurement and management according to embodiments herein.

FIG. 13 is a flowchart 1300 illustrating an example method according to embodiments. Note that there will be some overlap with respect to concepts as discussed above.

In processing block 1310, the controller 140 controls magnitudes of pressure in a first volume (such as chamber 150) and a second volume (such as chamber 130-2). The first volume is of a known magnitude (i.e., size, capacity, etc.). The second volume is of an unknown magnitude (i.e., size).

In processing block 1320, the controller 140 estimates a temperature of gas in the first volume and a temperature of gas in the second volume based on measurements of pressure in the first volume and measurements of pressure in the second volume.

In processing block 1330, the controller 140 calculates a magnitude of the second volume based measured pressures of the gases and estimated temperatures of gases in the first volume and the second volume.

Figure 14:
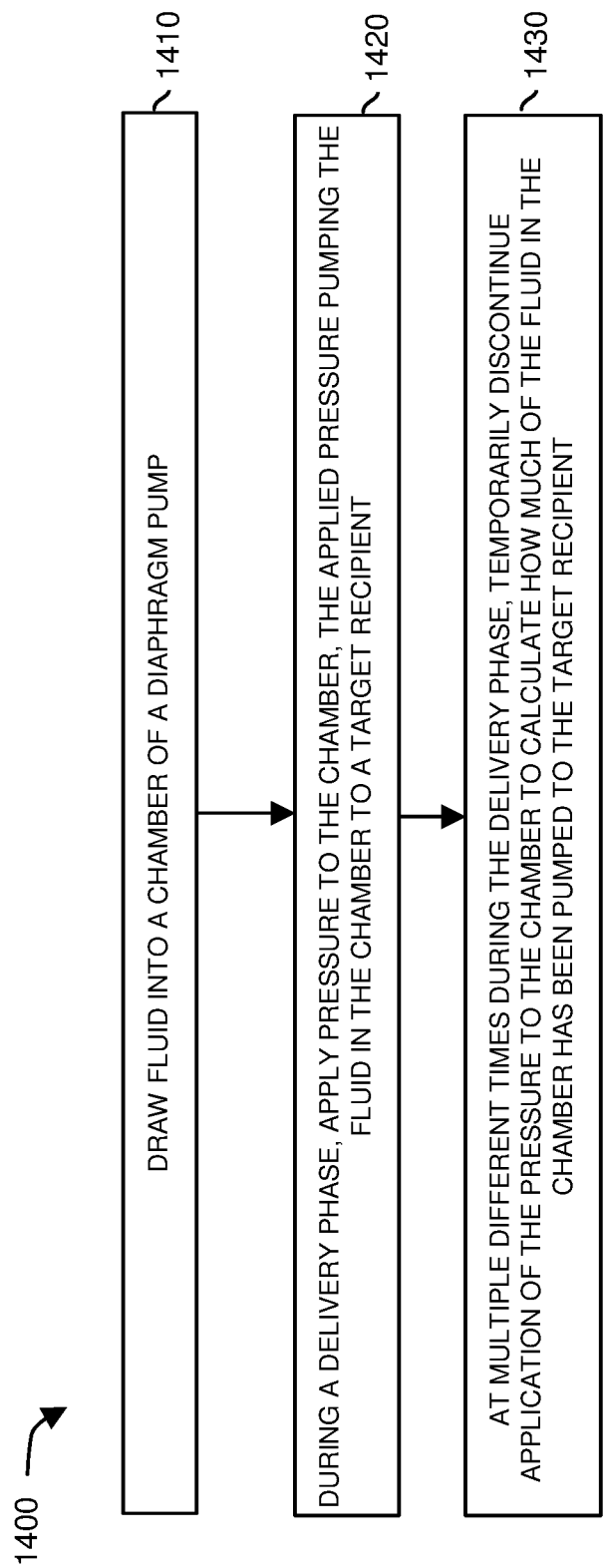

FIG. 14 is a flowchart 1400 illustrating an example method according to embodiments. Note that there will be some overlap with respect to concepts as discussed above.

In processing block 1410, the controller 140 draws fluid into a chamber of a diaphragm pump 130.

In processing block 1420, during a delivery phase, the controller 140 applies pressure to the chamber 130-1. The applied pressure pumps the fluid in the chamber 130-1 downstream to the positive displacement pump 184 and corresponding segment 1110.

In processing block 1430, at multiple different times during the delivery phase of delivering fluid to the positive displacement pump 184, the controller 140 temporarily modifies a magnitude of pressure applied to the chamber 130-2 (to discontinue or reduce a rate of fluid flow through diaphragm pump 130 to the positive displacement pump 184) to calculate how much of the fluid in the chamber 130-1 has been pumped to the positive displacement pump 184 and corresponding target recipient 108 in a respective sample window.

Figure 15:
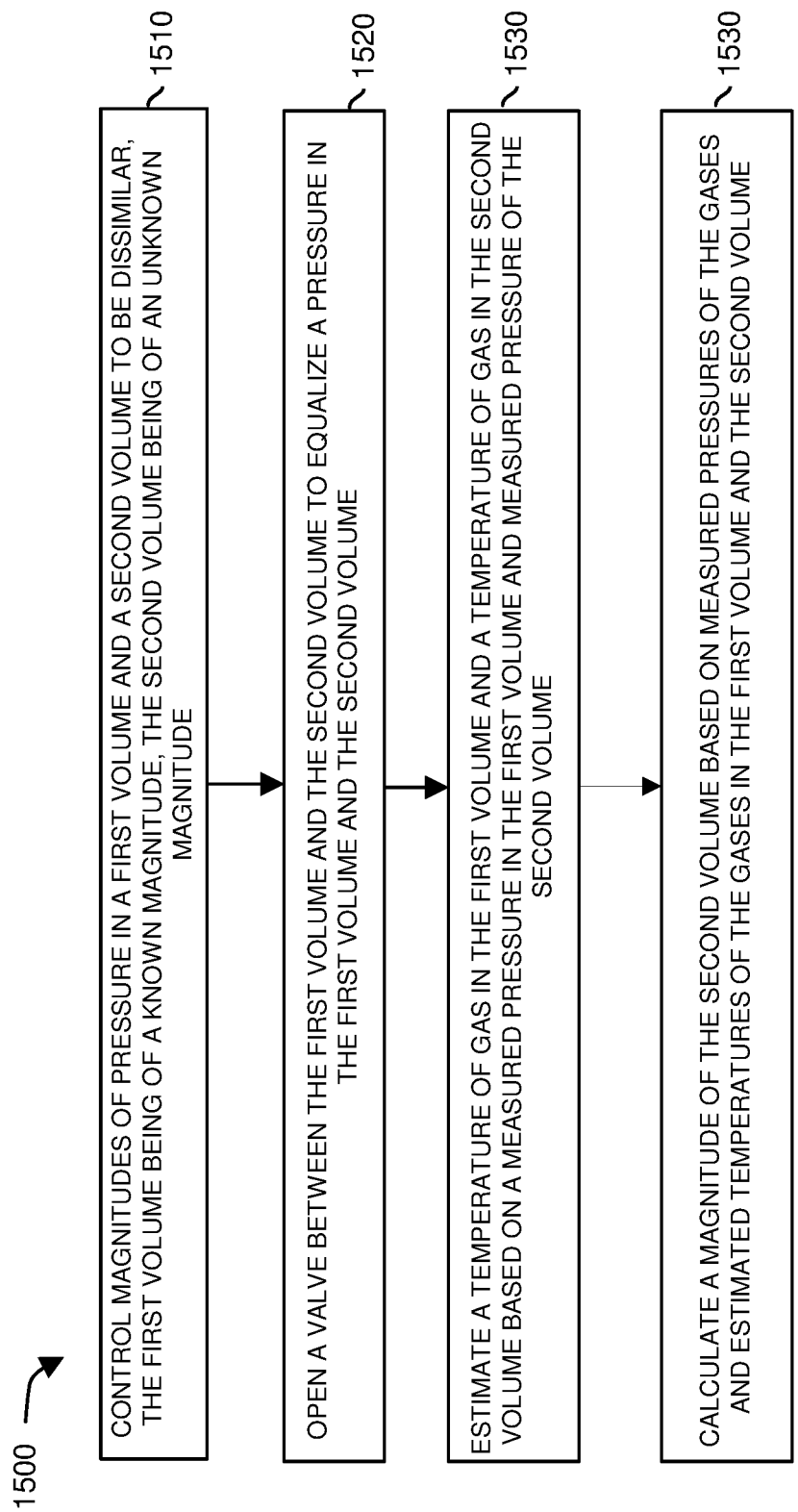

FIG. 15 is a flowchart 1500 illustrating an example method according to embodiments herein. Note that there will be some overlap with respect to concepts as discussed above.

In processing block 1510, the controller 140 controls magnitudes of pressure in a first volume (such as chamber 150) and a second volume (such as chamber 130-2) to be dissimilar. The first volume is of known magnitude. The second volume is of unknown magnitude.

In processing block 1520, the controller 140 initiates opening a valve 160-5 (while other valves are closed) between the first volume and the second volume to equalize a pressure in the first volume and the second volume.

In processing block 1530, the controller 140 estimates a temperature of gas in the first volume and a temperature of gas in the second volume based on a measured pressure in the first volume and measured pressure of the second volume.

In processing block 1540, the controller 140 calculates a magnitude of the second volume based on measured pressures of the gases and estimated temperatures of the gases in the first volume and the second volume.

Note again that techniques herein are well suited for use in fluid delivery systems. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention(s) has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A method comprising:
   drawing fluid into a chamber of a diaphragm pump;
   applying positive pressure to the chamber of the diaphragm pump to output the fluid in the chamber of the diaphragm pump downstream through a fluid conduit to a positive displacement pump; and
   during application of the pressure to the chamber of the diaphragm pump and outputting the fluid in the chamber downstream to the positive displacement pump, activating operation of the positive displacement pump to pump the fluid received at the positive displacement pump to a recipient, the method further comprising:
   controlling the positive displacement pump to provide continuous flow of the fluid to the recipient in a time window; and
   during each of multiple measurement windows that occur within the time window, temporarily adjusting a magnitude of the pressure applied to the chamber of the diaphragm pump to measure a respective portion of fluid remaining in the diaphragm pump.

2. The method as in claim 1, wherein the positive displacement pump is a peristaltic fluid pump, the peristaltic fluid pump including a peristaltic pump element in sweeping physical contact with a segment of the fluid conduit, the segment being an elastically deformable portion of conduit driven by the peristaltic fluid pump, the peristaltic pump element restricting passage of a flow of the fluid received from the diaphragm pump through the segment downstream to the recipient.

3. The method as in claim 2, wherein a pressure of the fluid in a first portion of the fluid conduit upstream of the peristaltic pump element between the peristaltic pump element and the diaphragm pump is different than a pressure of the fluid in a second portion of the fluid conduit disposed downstream of the peristaltic pump element between the peristaltic pump element and the recipient.

4. The method as in claim 2 further comprising:
   measuring a rate of fluid expelled from the chamber of the diaphragm pump downstream through the fluid conduit to the segment of fluid conduit; and
   controlling a rate of moving the peristaltic pump element to deliver the fluid to the recipient at a desired flow rate.

5. The method as in claim 1, wherein drawing the fluid into the chamber of the diaphragm pump includes cyclically receiving a respective quantum of the fluid from a fluid container into the chamber of the diaphragm pump, the fluid container disparately located with respect to the chamber of the diaphragm pump.

6. The method as in claim 1 further comprising:
   measuring a rate of the fluid being expelled from the chamber of the diaphragm pump downstream to the positive displacement pump, the positive displacement pump blocking a flow of the fluid received from the diaphragm pump; and
   utilizing the measured rate of fluid to control delivery of fluid from the positive displacement pump to the recipient as specified by a flow rate setting.

7. The method as in claim 1 further comprising:
   temporarily changing the pressure in the chamber to measure a rate of delivering the fluid from the chamber downstream through the fluid conduit to the positive displacement pump.

8. The method as in claim 1, wherein temporarily adjusting the magnitude of the pressure includes releasing gas from the diaphragm pump, the gas producing the pressure applied to the chamber prior to the releasing of the gas from the diaphragm pump.

9. The method as in claim 8 further comprising:
   utilizing the respective measured portions of fluid remaining in the diaphragm pump as measured during the multiple measurement windows to calculate a rate of fluid delivered by the positive displacement pump to the recipient.

10. The method as in claim 9, wherein a segment of the fluid conduit is a
    segment of elastically deformable conduit; and
    wherein the positive displacement pump includes a corresponding peristaltic pump element in physical contact with the segment of the elastically deformable conduit, the corresponding peristaltic pump element restricting a flow of the fluid received from the diaphragm pump through the positive displacement pump to the recipient.

11. The method as in claim 1, wherein the fluid conduit includes an elastically deformable segment of conduit, the method further comprising:
    drawing the fluid from a fluid source into the chamber of the diaphragm pump during a condition in which a peristaltic pump element of the positive displacement pump in physical contact with the elastically deformable segment of conduit blocks a flow of the fluid received from the diaphragm pump through the fluid conduit.

12. A fluid delivery apparatus comprising:
    a diaphragm pump;
    a positive displacement pump;
    a fluid conduit extending between the diaphragm pump and the positive displacement pump; and controller hardware, the controller hardware operable to:
  draw fluid into a chamber of the diaphragm pump;
  apply pressure to the chamber of the diaphragm pump to output the fluid in the chamber of the diaphragm pump downstream through the fluid conduit to the positive displacement pump; and
  during application of the pressure to the chamber and outputting the fluid in the chamber downstream, activate the positive displacement pump to pump the fluid from the positive displacement pump to a recipient;
  wherein the controller hardware is further operative to: control the positive displacement pump to provide continuous flow of fluid to the recipient; and during each of multiple measurement windows that occur within a time window, temporarily adjust a magnitude of the pressure applied to the chamber of the diaphragm pump to measure a respective portion of fluid remaining in the diaphragm pump.

13. The fluid delivery apparatus as in claim 12, wherein the positive displacement pump is a peristaltic fluid pump, the peristaltic fluid pump including a peristaltic pump element in sweeping physical contact with an elastically deformable segment of the fluid conduit, the peristaltic pump element operable to restrict a flow of the fluid received from the diaphragm pump through the elastically deformable segment downstream to the recipient.

14. The fluid delivery apparatus as in claim 13, wherein a pressure of the fluid in a first portion of the fluid conduit upstream of the peristaltic pump element between the peristaltic pump element and the diaphragm pump is different than a pressure of the fluid in a second portion of the fluid conduit disposed downstream of the peristaltic pump element between the peristaltic pump element and the recipient.

15. The fluid delivery apparatus as in claim 13, wherein the controller hardware is further operable to:
  measure a rate of fluid expelled from the chamber of the diaphragm pump downstream through the fluid conduit to the segment of fluid conduit; and
  control a rate of moving the peristaltic pump element to deliver the fluid from the positive displacement pump to the recipient at a desired flow rate.

16. The fluid delivery apparatus as in claim 12, wherein the controller hardware is further operable to:
  cyclically receive a respective quantum of the fluid from a fluid container into the chamber of the diaphragm pump at each of multiple fill times, the fluid container disparately located with respect to the chamber of the diaphragm pump.

17. The fluid delivery apparatus as in claim 12, wherein the controller is further operable to:
  measure a flow rate of the fluid being expelled from the chamber of the diaphragm pump downstream to the positive displacement pump, a mechanical pump element of the positive displacement pump blocking a flow of the fluid received from the diaphragm pump to the recipient; and
  utilize the measured flow rate of the fluid to control delivery of fluid from the positive displacement pump to the recipient as specified by a flow rate setting.

18. The fluid delivery apparatus as in claim 12, wherein the controller hardware is further operable to:
  at each of multiple measurement times between a first filling of the chamber and a subsequent time of drawing the fluid into the chamber from a fluid source, temporarily adjusting application of the pressure to the chamber to measure a rate of delivering the fluid from the chamber downstream to the positive displacement pump.

19. The fluid delivery apparatus as in claim 12, wherein the controller hardware is further operable to, during a respective temporary adjustment of measuring fluid flow, release the pressure applied to the chamber.

20. The fluid delivery apparatus as in claim 19, wherein the controller hardware is further operable to: utilize the respective measured portions of fluid remaining in the diaphragm pump as measured during the multiple measurement windows to calculate a rate of fluid delivered by the positive displacement pump to the recipient.

21. The fluid delivery apparatus as in claim 20, wherein a segment of the fluid conduit is a segment of elastically deformable conduit; and
  wherein the positive displacement pump is a peristaltic fluid pump including a corresponding peristaltic pump element in physical contact with the segment of elastically deformable conduit, the pump element restricting a flow of the fluid received from the diaphragm pump through the elastically deformable segment to the recipient.

22. The fluid delivery apparatus as in claim 12, wherein the controller hardware is further operable to:
  draw the fluid from a fluid source into the chamber of the diaphragm pump during a condition in which the positive displacement pump blocks a flow of the fluid received from the diaphragm pump to the recipient.

23. Computer-readable storage hardware having instructions stored thereon,
  the instructions, when carried out by computer processor hardware,
  cause the computer processor hardware to:
  draw fluid into a chamber of a diaphragm pump;
  apply pressure to the chamber of the diaphragm pump to output the fluid in the chamber of the diaphragm pump downstream through the fluid conduit to a positive displacement pump;
  during application of the pressure to the chamber and outputting the fluid in the chamber downstream to the positive displacement pump, activate the positive displacement pump to pump the fluid from the positive displacement pump to a recipient; and
  wherein the computer processor hardware is further operative to: control the positive displacement pump to provide continuous flow of fluid to the recipient in a time window, and during each of multiple measurement windows that occur within the time window, temporarily adjust a magnitude of the pressure applied to the chamber of the diaphragm pump to measure a respective portion of fluid remaining in the diaphragm pump.

24. The method as in claim 1 further comprising:
  during a fluid measurement window:
    halting movement of a pump element of the positive displacement pump; and
    temporarily adjusting the pressure applied to the chamber of the diaphragm pump to measure a respective portion of fluid remaining in the chamber of the diaphragm pump.

25. The fluid delivery apparatus as in claim 12, wherein the controller hardware is further operable to:

stop movement of a pump element of the positive displacement pump; and while the pump element is stopped, temporarily adjust the pressure applied to the chamber of the diaphragm pump to measure a respective portion of fluid remaining in the diaphragm pump.

26. A method comprising:

drawing fluid into a chamber of a diaphragm pump;

applying positive pressure to the chamber of the diaphragm pump to output the fluid in the chamber of the diaphragm pump downstream through a fluid conduit to a positive displacement pump;

during application of the pressure to the chamber of the diaphragm pump and outputting the fluid in the chamber downstream to the positive displacement pump, activating operation of the positive displacement pump to pump the fluid received at the positive displacement pump to a recipient; and wherein a pressure of the fluid in a first portion of the fluid conduit upstream of the positive displacement pump between the positive displacement pump and the diaphragm pump is less than a pressure of the fluid in a second portion of the fluid conduit disposed downstream of the positive displacement pump between the positive displacement pump and the recipient.

27. The apparatus as in claim 12, wherein the fluid conduit is a first fluid conduit; and wherein a pressure of the fluid in the first fluid conduit between the diaphragm pump and the positive displacement pump is less than a pressure of the fluid in a second fluid conduit disposed between the positive displacement pump and the recipient, the positive displacement pump operative to output the fluid to the second fluid conduit.

28. The apparatus as in claim 12, wherein the controller hardware is further operative to:

monitor a pressure of the fluid in the fluid conduit between the diaphragm pump and the positive displacement pump.

29. The apparatus as in claim 12, wherein the controller hardware is further operative to:

measure delivery of the fluid to the positive displacement pump based upon measurements of a respective remaining portion of the fluid in the chamber of the diaphragm pump for each of multiple sample times.

30. The method as in claim 1, wherein a flow rate of the fluid through the diaphragm pump to the positive displacement pump varies with respect to a flow of the fluid outputted from the positive displacement pump to the recipient.

31. The fluid delivery apparatus as in claim 12, wherein the controller hardware is further operable to, during a respective temporary adjustment of measuring fluid flow and operating the positive displacement pump to deliver the fluid to the recipient, release the pressure applied to the chamber.

32. The fluid delivery apparatus as in claim 12, wherein the controller hardware is further operable to: utilize respective measured portions of fluid remaining in the diaphragm pump as measured during multiple measurement windows to calculate and control a rate of fluid delivered by the positive displacement pump to the recipient.

33. The fluid delivery apparatus as in claim 12, wherein a segment of the fluid conduit is a segment of elastically deformable conduit; and wherein the positive displacement pump is a peristaltic fluid pump including a corresponding peristaltic pump element in physical contact with the segment of the fluid conduit, the pump element restricting a flow of the fluid received from the diaphragm pump through the segment to the recipient.

34. The method as in claim 12, wherein the controller hardware is operative to control a rate of delivering the fluid through the positive displacement pump to the recipient based on measured flow of the fluid through the diaphragm pump.

35. A fluid delivery apparatus comprising:

a diaphragm pump;

a positive displacement pump;

a fluid conduit extending between the diaphragm pump and the positive displacement pump; and controller hardware, the controller hardware operable to:

draw fluid into a chamber of the diaphragm pump;

apply pressure to the chamber of the diaphragm pump to output the fluid in the chamber of the diaphragm pump downstream through the fluid conduit to the positive displacement pump; and during application of the pressure to the chamber and outputting the fluid in the chamber downstream, activate the positive displacement pump to pump the fluid from the positive displacement pump to a recipient; and wherein a pressure of the fluid in a first portion of the fluid conduit upstream of the positive displacement pump between the positive displacement pump and the diaphragm pump is less than a pressure of the fluid in a second portion of the fluid conduit disposed downstream of the positive displacement pump between the positive displacement pump and the recipient.

* * * * *